US010316322B2

(12) United States Patent
Groff et al.

(10) Patent No.: US 10,316,322 B2
(45) Date of Patent: Jun. 11, 2019

(54) **HIGH GROWTH CAPACITY AUXOTROPHIC *ESCHERICHIA COLI* AND METHODS OF USE**

(71) Applicant: Sutro Biopharma, Inc., South San Francisco, CA (US)

(72) Inventors: Dan Groff, Alameda, CA (US); Patrick Rivers, Oakland, CA (US); Stuart Bussell, Carlsbad, CA (US); Alexander Steiner, San Francisco, CA (US)

(73) Assignee: Sutro Biopharma, Inc., South San Francisco, CA (US)

( * ) Notice: Subject to any disclaimer, the term of this patent is extended or adjusted under 35 U.S.C. 154(b) by 0 days.

(21) Appl. No.: 15/319,513

(22) PCT Filed: Jun. 30, 2015

(86) PCT No.: PCT/US2015/038529
§ 371 (c)(1),
(2) Date: Dec. 16, 2016

(87) PCT Pub. No.: WO2016/004024
PCT Pub. Date: Jan. 7, 2016

(65) Prior Publication Data
US 2017/0191070 A1 Jul. 6, 2017

Related U.S. Application Data

(60) Provisional application No. 62/020,043, filed on Jul. 2, 2014.

(51) Int. Cl.
*C12N 15/70* (2006.01)
*C12N 15/63* (2006.01)
*C12N 15/79* (2006.01)
*C12N 1/20* (2006.01)
*C12P 21/02* (2006.01)

(52) U.S. Cl.
CPC .............. *C12N 15/70* (2013.01); *C12N 1/20* (2013.01); *C12P 21/02* (2013.01)

(58) Field of Classification Search
None
See application file for complete search history.

(56) References Cited

U.S. PATENT DOCUMENTS

| 5,747,308 | A | 5/1998 | Bebbington et al. | |
|---|---|---|---|---|
| 6,291,245 | B1 | 9/2001 | Kopetzki et al. | |
| 2003/0148475 | A1* | 8/2003 | Ptitsyn | C12N 9/1025 435/114 |
| 2009/0042251 | A1 | 2/2009 | Scholz et al. | |
| 2009/0155844 | A1 | 6/2009 | Yokoyama et al. | |
| 2009/0325230 | A1 | 12/2009 | Schneider et al. | |
| 2011/0177566 | A1 | 7/2011 | Savrasova et al. | |
| 2012/0115187 | A1* | 5/2012 | Retallack | C12N 15/65 435/69.1 |

FOREIGN PATENT DOCUMENTS

| EP | 0972838 A1 | 1/2000 |
|---|---|---|
| EP | 1170361 A2 | 1/2002 |

OTHER PUBLICATIONS

PCT/US2015/038529, "International Search Report and Written Opinion", dated Oct. 2, 2015, 14 pages.
Bozouklian et al., "Cloning and Characterization of the glnA Gene of *Azospirillum brasilense* Sp7", Annales De L'institut Pasteur/Microbiologie, vol. 137 B, No. 1, Jul. 8, 1986, pp. 3-18.
Groff et al., "Engineering Toward a Bacterial "Endoplasmic Reticulum" for the Rapid Expression of Immunoglobulin Proteins", MABS, vol. 6, No. 3, 2014, pp. 671-678.
Howarth et al., "Cysteine Biosynthesis in Higher Plants; A New Member of the *Arabidopsis thaliana* Serine Acetyltransferase Small Gene-Family Obtained by Functional Complementation of an *Escherichia coli* Cysteine Auxotroph", Biochimica et Biophysica Acta, Gene Structure and Expression, vol. 1350, Jan. 1, 1997, pp. 123-127.
Kumada et al., "*Streptomyces hygroscopicus* Has Two Glutamine Synthetase Genes", Journal of Bacteriology, vol. 172, No. 9, Sep. 1, 1990, pp. 5343-5351.
Mountain et al., "Gene Sequence Encoding Early Enzymes of Arginine Synthesis within a Cluster in *Bacillus subtilis*, as Revealed by Cloning in *Escherichia coli*", Journal of Bacteriology, vol. 165, No. 3, Mar. 1, 1986, pp. 1026-1028.
Parker et al., "Evidence for Redundancy in Cysteine Biosynthesis in *Rhizobium leguminosarum* RL3841: analysis of a cysE Gene Encoding Serine Acetyltransferase", Microbiology, vol. 147, No. 9, Sep. 1, 2001, pp. 2553-2560.
Porter et al., "Genes from the Cyanobacterium *Agmenellum quadruplicatum* Isolated by Complementation: Characterization and Production of Merodiploids", Gene, vol. 41, No. 2-3, Jan. 1, 1986, pp. 249-260.
Takagi et al., "PCR Random Mutagenesis into *Escherichia coli* Serine Acetyltransferase: Isolation of the Mutant Enzymes that Cause Overproduction of L-Cysteine And L-Cystine Due to the Desensitization to Feedback Inhibition", FEBS Letters, vol. 452, No. 3, Jun. 11, 1999, pp. 323-327.
Urano et al., "Molecular Cloning and Functional Characterization of cDNAs Encoding Cysteine Synthase and Serine Acetyltransferase that may be Responsible for High Cellular Cysteine Content in *Allium tuberosum*", Gene, vol. 257, No. 2, Oct. 31, 2000, pp. 269-277.
EP15814265.3, "Extended European Search Report", dated Dec. 18, 2017, 14 pages.

* cited by examiner

*Primary Examiner* — Channing S Mahatan
(74) *Attorney, Agent, or Firm* — Kilpatrick Townsend & Stockton LLP

(57) ABSTRACT

This invention provides high growth capacity strains of auxotrophic *Escherichia coli* and methods for generating thereof. The high growth capacity strains express a complementing auxotrophic plasmid that allows the strain to grow in the absence of the auxotrophic amino acid. Also, provided herein is a method for preparing a bacterial cell extract of a high growth capacity strain of auxotrophic *Escherichia coli* for use in an in vitro protein expression.

23 Claims, 7 Drawing Sheets
Specification includes a Sequence Listing.

SEQUENCE LISTING

```
<160> NUMBER OF SEQ ID NOS: 11

<210> SEQ ID NO 1
<211> LENGTH: 4
<212> TYPE: DNA
<213> ORGANISM: Artificial Sequence
<220> FEATURE:
<223> OTHER INFORMATION: synthetic oligonucleotide

<400> SEQUENCE: 1 agga                                                                      4

<210> SEQ ID NO 2
<211> LENGTH: 4
<212> TYPE: DNA
<213> ORGANISM: Artificial Sequence
<220> FEATURE:
<223> OTHER INFORMATION: synthetic oligonucleotide

<400> SEQUENCE: 2 cuag                                                                      4

<210> SEQ ID NO 3
<211> LENGTH: 4
<212> TYPE: DNA
<213> ORGANISM: Artificial Sequence
<220> FEATURE:
<223> OTHER INFORMATION: synthetic oligonucleotide

<400> SEQUENCE: 3 uaga                                                                      4

<210> SEQ ID NO 4
<211> LENGTH: 4
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(4)
<223> OTHER INFORMATION: N is A, C, G, or U

<400> SEQUENCE: 4 uagn                                                                      4

<210> SEQ ID NO 5
<211> LENGTH: 4
<212> TYPE: DNA
<213> ORGANISM: Artificial Sequence
<220> FEATURE:
<223> OTHER INFORMATION: synthetic oligonucleotide

<400> SEQUENCE: 5 cccu                                                                      4

<210> SEQ ID NO 6
<211> LENGTH: 5
<212> TYPE: DNA
<213> ORGANISM: Artificial Sequence
<220> FEATURE:
<223> OTHER INFORMATION: synthetic oligonucleotide

<400> SEQUENCE: 6 aggac                                                                     5
```

```
<210> SEQ ID NO 7
<211> LENGTH: 5
<212> TYPE: DNA
<213> ORGANISM: Artificial Sequence
<220> FEATURE:
<223> OTHER INFORMATION: synthetic oligonucleotide

<400> SEQUENCE: 7 ccccu                                                               5

<210> SEQ ID NO 8
<211> LENGTH: 5
<212> TYPE: DNA
<213> ORGANISM: Artificial Sequence
<220> FEATURE:
<223> OTHER INFORMATION: synthetic oligonucleotide

<400> SEQUENCE: 8 cccuc                                                               5

<210> SEQ ID NO 9
<211> LENGTH: 5
<212> TYPE: DNA
<213> ORGANISM: Artificial Sequence
<220> FEATURE:
<223> OTHER INFORMATION: synthetic oligonucleotide

<400> SEQUENCE: 9 cuaga                                                               5

<210> SEQ ID NO 10
<211> LENGTH: 5
<212> TYPE: DNA
<213> ORGANISM: Artificial Sequence
<220> FEATURE:
<223> OTHER INFORMATION: synthetic oligonucleotide

<400> SEQUENCE: 10 cuacu                                                               5

<210> SEQ ID NO 11
<211> LENGTH: 5
<212> TYPE: DNA
<213> ORGANISM: Artificial Sequence
<220> FEATURE:
<223> OTHER INFORMATION: synthetic oligonucleotide

<400> SEQUENCE: 11 uaggc                                                               5
```

HIGH GROWTH CAPACITY AUXOTROPHIC *ESCHERICHIA COLI* AND METHODS OF USE

CROSS-REFERENCES TO RELATED APPLICATIONS

This application is a U.S. National Phase under 35 USC 371 of PCT Application No. PCT/US2015/038529, filed Jun. 30, 2015, which claims priority to U.S. Provisional Application No. 62/020,043, filed Jul. 2, 2014, the disclosures of which are hereby incorporated by reference in their entirety for all purposes.

REFERENCE TO SEQUENCE LISTING

This application includes a Sequence Listing as a text file named "Sequence Listing for 091200-006310US-1032778.txt" created Dec. 14, 2016, and containing 2,660 bytes. The material contained in this text file is incorporated by reference in its entirety for all purposes.

BACKGROUND OF THE INVENTION

The expression of proteins in bacterial cell free synthesis systems is a well established technique for expressing recombinant target proteins. Extracts can be made from bacteria expressing or overexpressing proteins of interest to provide bacterial cell free synthesis systems having altered properties depending on the protein. However, overexpression of proteins during bacterial growth frequently results in slower growth rates for the bacteria and lower protein synthetic activity in extracts prepared from the bacteria.

This invention provides for high growth capacity strains of auxotrophic *Escherichia coli*. These strains find use in cell free synthesis systems where ribosomal density, as reflected by high growth capacity, is an economically important property of desired bacteria. The ability of bacteria to maintain high growth capacity after recombinant inactivation of enzymes is unpredictable.

BRIEF SUMMARY OF THE INVENTION

The present disclosure provides methods for producing auxotrophic bacterial strains and complemented auxotrophic strains for the expression of biologically active and/or properly folded proteins of interest in a cell free synthesis system. The cell free synthesis system comprises a bacterial extract having an active oxidative phosphorylation system and the components necessary for cell free protein synthesis. The complemented auxotrophic strains contain an expression plasmid that can restore the ability of the strain to grow in media lacking the growth requiring amino acid (e.g., auxotrophic amino acid). In some embodiments, an exogenous protein chaperone is also expressed by the auxotroph. In other embodiments, an exogenous tRNA is also expressed by the auxotroph.

In one aspect, provided herein is a method for maintaining an auxotrophic selection plasmid within the cytosol of a population of *E. coli* cells, wherein the doubling rate of the cell population is less than 60 minutes, e.g., 59 minutes, 58 minutes, 57 minutes, 56 minutes, 55 minutes, 54 minutes, 53 minutes, 52 minutes, 51 minutes, 50 minutes, 49 minutes, 48 minutes, 47 minutes, 46 minutes, 45 minutes, 44 minutes, 43 minutes, 42 minutes, 41 minutes, 40 minutes, or less. The method includes: (i) inactivating a gene in the *E. coli* cell wherein the gene is necessary for the biosynthesis of an essential amino acid selected from the group consisting of glutamine, cysteine, and arginine to yield an auxotrophic strain of *E. coli*; (ii) transforming the auxotrophic strain of *E. coli* with the auxotrophic selection plasmid having an expression cassette comprising a constitutive promoter operably linked to a gene encoding an enzyme able to restore the ability of the strain to grow in the absence of the essential amino acid; and (iii) culturing the transformed *E. coli* of step (ii) in a growth media lacking the essential amino acid, thereby applying selective pressure to maintain the auxotrophic selection plasmid within the cytosol of the *E. coli* cell population, wherein the doubling rate of the *E. coli* cell population is less than 60 minutes. The *E. coli* cell population can be lysed after culturing.

In some embodiments, the inactivated gene is selected from the group consisting of glnA, cysE and argA. The inactivated gene can be glnA. The inactivated gene can be cysE. Alternatively, the inactivated gene can be argA.

The auxotrophic selection plasmid described herein can be a multicopy plasmid, such as a high, medium or low copy number plasmid. Optionally, the plasmid can include a strong constitutive promoter. The auxotrophic selection plasmid can further include an expression cassette comprising a gene encoding a chaperone protein or a tRNA. In some instances, the chaperone protein is selected from the group consisting of DsbA, DsbB, DsbC, DsbD, FkpA, SlyD, and a combination thereof. The tRNA can be a suppressor tRNA.

In some embodiments, the *E. coli* cells have an inactivated gene encoding a protein selected from the group consisting of tryptophanase, arginine decarboxylase, L-serine deaminase and gamma-glutamylcysteine synthase.

The growth media for culturing the *E. coli* cells can be a defined media.

In another aspect, provided herein is a high-growth capacity, auxotrophic strain of *E. coli* cells, wherein the strain: (i) has an inactivated gene necessary for the synthesis of an essential amino acid selected from the group consisting of glutamine, cysteine, and arginine; (ii) is transformed with an auxotrophic selection plasmid having an expression cassette comprising a constitutive promoter operably linked to a gene encoding an enzyme able to restore the ability of the strain to grow in the absence of the essential amino acid; and (iii) has a doubling rate of less than 60 minutes in a growth media lacking the essential amino acid. In some instances, the doubling rate is less than 60 minutes e.g., 59 minutes, 58 minutes, 57 minutes, 56 minutes, 55 minutes, 54 minutes, 53 minutes, 52 minutes, 51 minutes, 50 minutes, 49 minutes, 48 minutes, 47 minutes, 46 minutes, 45 minutes, 44 minutes, 43 minutes, 42 minutes, 41 minutes, 40 minutes, or less.

The inactivated gene of the strain can be selected from the group consisting of glnA, cysE and argA. In some embodiments, the inactivated gene is glnA. In other embodiments, the inactivated gene is cysE. In yet other embodiments, the inactivated gene is argA.

The *E. coli* cells can have an inactivated gene encoding a protein selected from the group consisting of tryptophanase, arginine decarboxylase, L-serine deaminase and gamma-glutamylcysteine synthase. The auxotrophic selection plasmid further includes an expression cassette comprising a gene encoding a chaperone protein or a tRNA. The chaperone protein can be DsbA, DsbB, DsbC, DsbD, FkpA, SlyD, or a combination thereof. In some embodiments, the tRNA is a suppressor tRNA.

In another aspect, provided herein is a method for preparing a bacterial cell extract for use in an in vitro protein expression reaction. The method includes the steps of: (i)

culturing an *E. coli* cell in a growth media lacking an essential amino acid selected from the group consisting of glutamine, cysteine, and arginine, wherein (a) a gene that is necessary for the biosynthesis of the essential amino acid in the *E. coli* cell has been inactivated; (b) the *E. coli* cell comprises an auxotrophic selection plasmid having an expression cassette comprising a constitutive promoter operably linked to a gene encoding an enzyme able to restore the ability of the strain to grow in the absence of the essential amino acid; and (c) the doubling rate of a population of the *E. coli* cell is less than 60 minutes, e.g., 59 minutes, 58 minutes, 57 minutes, 56 minutes, 55 minutes, 54 minutes, 53 minutes, 52 minutes, 51 minutes, 50 minutes, 49 minutes, 48 minutes, 47 minutes, 46 minutes, 45 minutes, 44 minutes, 43 minutes, 42 minutes, 41 minutes, 40 minutes, or less; and (ii) preparing a bacterial cell extract of the culture. The step of preparing the bacterial cell extract of the culture (step ii) can include lysing the *E. coli* cell.

In some embodiments, the inactivated gene is selected from the group consisting of glnA, cysE, and argA. The inactivated gene can be glnA. The inactivated gene can be cysE. The inactivated gene can be argA.

The *E. coli* cell can have an inactivated gene encoding a protein selected from the group consisting of tryptophanase, arginine decarboxylase, L-serine deaminase and gamma-glutamylcysteine synthase.

In some embodiments, the auxotrophic selection plasmid is a multicopy plasmid, such as a high, medium or low copy number plasmid.

In some embodiments, the auxotrophic selection plasmid further includes an expression cassette comprising a gene encoding a chaperone protein or a tRNA. The chaperone protein can be selected from the group consisting of DsbA, DsbB, DsbC, DsbD, FkpA, SlyD, and a combination thereof. The tRNA can be a suppressor tRNA.

Other objects, features, and advantages of the present invention will be apparent to one of skill in the art from the following detailed description and figures.

BRIEF DESCRIPTION OF THE DRAWINGS

FIG. 1A shows the gene deletion of the argA auxotrophic *E. coli*. FIG. 1B shows the gene deletion of the cysE auxotrophic *E. coli*. FIG. 1C shows the gene deletion of the glnA auxotrophic *E. coli*.

FIG. 4A provides the $OD_{600}$ plotted versus time. For FIG. 4B, the glnA auxotrophic strain (e.g., glnA knockout strain) was excluded and the growth data was plotted on a log scale graph.

DETAILED DESCRIPTION OF THE INVENTION

I. Introduction

Figure 1A:
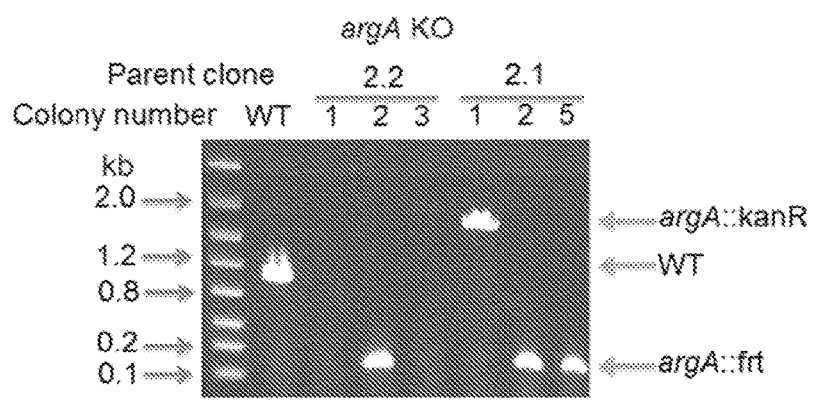
FIGS. 1A-C show colony PCR verification of auxotrophic gene deletion. The area around each gene was amplified using colony with primers flanking the 5' and 3' regions of each gene.

In cell free synthesis (CFS) reaction vessels intended for commercial production of proteins of interest, the health and vigor of the bacteria giving rise to the CFS lysate are critical to the success of the downstream production of protein. If the bacteria lack vigor and robustness, their ribosomal density decreases and the production of a target protein of interest by CFS will decline (Zawada and Swartz, *Biotechnol Bioeng*, 94(4):618-624 (2006)). The vigor and robustness of a bacteria strain are directly reflected by the growth rate of the bacterial population. Growth rate is measured by the doubling time or the time needed to increase the population of cells by 100%.

In commercial CFS, bacteria having doubling rates of less than 60 minutes, and more preferably less than 40 minutes, are preferred. These preferred strains are referred to as high growth capacity strains. Described herein is the creation of high growth capacity *E. coli* strains based on glnA, cysE or argA auxotrophic strains that have been modified to carry a complementing glnA, cysE or argA plasmid, respectively. Unpredictably, the high capacity growth rates of the subsequent *E. coli* mutants were maintained when the cells were cultured in complete media in the presence of the complementing plasmid.

When grown in complete media, i.e., containing the essential amino acid synthesized by the deleted gene, the auxotrophic cells, particularly the glnA mutant, lacked expected levels of vigor. However, expression of the complementing plasmid can restore cellular vigor in the cells grown in either the complete or incomplete media. The fact that the auxotrophic strains unrestored did not grow well in complete media was unexpected and economically advantageous. The maintenance of selective pressure on the phenotype restoring plasmid in the presence of complete media is economically advantageous because defined media is more expensive than undefined media.

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "auxotrophic strain of *E. coli*," "auxotrophic cell" or "auxotroph" refers to a mutant *E. coli* cell or strain that is unable to synthesize a molecule, amino acid, protein, nutrient, organic compound, etc. required for its growth and/or metabolism on its own.

"Doubling time" or "doubling rate" refers to the measure of time required for a population of cells to increase by 100% or double in number.

"Essential amino acid" refers to a growth requiring amino acid wherein the absence of the amino acid reduces growth rate in the auxotrophic mutant bacteria by at least 3-fold over the wild-type bacteria in the same media.

The term "auxotrophic amino acid" refers to an amino acid that is required by an auxotrophic cell to grow. The absence of the auxotrophic amino acid in the growth medium reduces the growth rate of the auxotrophic mutant bacteria by, for example, at least 3-fold over the wild-type bacteria in the same media. For example, an argA auxotroph requires the presence of arginine in the media for growth. For this mutant, arginine is an auxotrophic amino acid.

The term "auxotrophic selection plasmid" or "complementing plasmid" refers to a plasmid that includes a gene encoding an enzyme that can restore the ability of an auxotroph to grow in the absence of its auxotrophic amino acid. The plasmid can be introduced and expressed in the auxotroph.

The term "inactivating a gene" refers to a process of disrupting or inactivating the expression or function of a gene or a transcript thereof.

The term "gene is necessary for the biosynthesis of glutamine" refers to any gene that encodes a protein such as a substrate or enzyme that is useful for the biosynthesis of the amino acid glutamine, including precursors and variants of glutamine.

The term "gene is necessary for the biosynthesis of cysteine" refers to any gene that encodes a protein such as a substrate or enzyme that is useful for the biosynthesis or production of the amino acid cysteine, including precursors and variants of cysteine.

The term "gene is necessary for the biosynthesis of arginine" refers to any gene that encodes a protein such as a substrate or enzyme that is useful for the biosynthesis of the amino acid arginine, including precursors and variants of arginine.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The phrase "nucleic acid sequence encoding" or a "nucleic acid coding sequence" refers to a nucleic acid which directs the expression of a specific protein or peptide. Such nucleic acid sequences include both the DNA strand sequence that is transcribed into RNA, and the RNA sequence that is translated into protein. The nucleic acid sequences include both the full length nucleic acid sequences as well as non-full length sequences derived from the full length sequences. A coding sequence can include degenerate codons (relative to the native sequence) or sequences that provide codon preference in a specific host cell.

The terms "polypeptide," "peptide," and "protein" are used interchangeably herein to denote to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "suppressor tRNA" refers to a tRNA that alters the reading of a mRNA in a particular translation system (e.g., cell-free protein synthesis system), such as by allowing for the incorporation of non-natural amino acids into a growing polypeptide chain in response to a specific codon, e.g., a stop codon, a rare codon, a four- or more base codon, and the like.

The term "operably linked" refers to nucleic acid sequences that are linked contiguously such that the first nucleic acid sequence (e.g., a promoter) affects the function of the second nucleic acid sequence (e.g., a gene).

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators). Generally, an expression cassette is inserted into an expression vector (e.g., a plasmid) to be introduced into a host cell.

The term "constitutive promoter" refers to a nucleic acid sequence that, under appropriate conditions, allows for unregulated and continual transcription of a nucleic acid sequence or gene that is operably connected or linked to the promoter sequence. The appropriate conditions include transcription factors, such as RNA polymerase, that bind to the promoter sequence, and ribonucleotides that are incorporated into the transcribed RNA. Constitutive promoters are typically unregulated promoters in that they promote continual transcription under normal cellular conditions.

The term "strong promoter" refers to promoter (e.g., region of DNA that initiates transcription of a gene) that can drive transcription of RNA from adjacent DNA (gene) such that more copies of RNA are generated compared to a weaker promoter. A strong promoter can have a promoter activity of about >50 Miller units in *E. coli*, when cloned, for example into the multiple cloning site of a plasmid, such as pAK80. A "medium promoter" can have a promoter activity of about 8-50 Miller units in *E. coli* and a "weak" promoter can have a promoter activity of <8 Miller units in *E. coli*, when all compared using the same reporter expression system, such as the β-galactosidase (β-gal) assay, as described in, e.g., Miller. *Experiments in Molecular Genetics*. Cold Spring Harbor, N.Y., Cold Spring Harbor Laboratory, 1972.

The term "defined media" or "chemically defined media" refers to a chemically synthetic growth media, such as a liquid growth media for propagating an organism, such as bacteria. In contrast, an undefined media refers to a complex medium formulated with components of natural origin.

The term "multicopy plasmid" refers to a plasmid that when transformed into a host cell is present in on average more than one copy. For instance, a multicopy plasmid exists in multiple copies, e.g., at least 2 or more copies, in a single host cell.

The term "transforming," "transformed" or "transformation" refers to the introduction of a nucleic acid into a cell by non-viral-based methods. The nucleic acid molecules may be gene sequences encoding complete proteins or functional portions thereof. See, e.g., Sambrook et al., 1989, *Molecular Cloning: A Laboratory Manual*, 18.1-18.88.

The terms "culture," "culturing," "grow," "growing," "maintain," "maintaining," "expand," "expanding," etc., when referring to cell culture itself or the process of culturing, can be used interchangeably to mean that a cell is maintained outside its normal environment under controlled conditions, e.g., under conditions suitable for survival. Cultured cells are allowed to survive, and culturing can result in cell growth, stasis, differentiation or division. The term does not imply that all cells in the culture survive, grow, or divide, as some may naturally die or senesce.

The term "selective pressure" refers to a force, pressure or condition that is applied to a population (e.g., a population of cells) that results in differential fitness or survival based on a preselected trait. For instance, applying antibiotic selective pressure includes culturing cells in the presence of an antibiotic of interest. Auxotrophic selective pressure can include culturing an auxotrophic cell in the absence of the auxotrophic amino acid.

The term "bacterial derived cell free extract," "bacterial cell extract," "bacterial extract" or "cell free extract" refers to a preparation of an in vitro reaction mixture able to transcribe DNA into mRNA and/or translate mRNA into polypeptides. The mixture includes ribosomes, ATP, amino acids, and tRNAs. The extract may be derived directly from lysed bacteria, from purified components or combinations of both.

The term "bacterial cell free synthesis system," "cell free synthesis system" "or "in vitro protein expression reaction" refers to the in vitro synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc.; and co-factors, enzymes and other reagents that are necessary for protein synthesis, e.g. ribosomes, uncharged tRNAs, tRNAs charged with unnatural amino acids, polymerases, transcriptional factors, tRNA synthetases, etc.

The term "chaperone protein" generally refers to a protein (e.g., a recombinant protein chaperone) that assists in the non-covalent folding and/or unfolding or the assembly and/or disassembly of polypeptides. In some embodiments, the chaperone protein is not normally expressed by the bacterial strain used to prepare the bacterial extract, or a recombinant protein chaperone that is expressed by a nucleic acid construct that is not present in the native bacterial strain. For example, if the native bacterial strain used to prepare the bacterial extract naturally expresses low levels of the endogenous protein chaperone (e.g., at levels not sufficient to improve the expression levels of a biologically active protein of interest), the exogenous protein chaperone can be expressed from a non-native nucleic acid construct, such that the nucleic acid sequences encoding the exogenous protein chaperone are under the control of different regulatory sequences than the endogenous sequences encoding the chaperone. For example, the protein chaperones DsbC and FkpA are naturally occurring *E. coli* proteins, but their expression levels are below the limit of detection using the ELISA assays described herein to detect proteins in bacterial extracts. Thus, the term "exogenous" is synonymous with "heterologous," which refers to a protein chaperone not normally expressed by the bacterial strain used to prepare the bacterial extract, or a nucleic acid encoding the protein chaperone that is not present in the native bacterial strain. In some embodiments, the term refers to recombinant protein chaperones that are added to a bacterial cell free extract, and thus are not expressed by the bacteria from which the extract was made.

As used herein, the following terms have the meanings ascribed to them unless specified otherwise.

III. General Methods

Unless defined otherwise, all technical and scientific terms used herein have the meaning commonly understood by one of ordinary skill in the art to which this invention belongs. Practitioners are particularly directed to Sambrook et al., *Molecular Cloning*, 2nd edition, Cold Spring Harbor Laboratory Press, (1989), and Ausubel, F. M., et al., *Current Protocols in Molecular Biology*, John Wiley & Sons, New York (2012), which are incorporated herein by reference, for definitions and terms of the art. Standard methods also appear in Bindereif, Schon, & Westhof (2005), *Handbook of RNA Biochemistry*, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Sambrook, J., (Id.); Ausubel, F. M., et al., (Id.); Berger and Kimmel, *Guide to Molecular Cloning Techniques, Methods in Enzymology* (Volume 152 Academic Press, Inc., San Diego, Calif. 1987); and *PCR Protocols: A Guide to Methods and Applications* (Academic Press, San Diego, Calif. 1990), which are incorporated by reference herein.

Methods for protein purification, chromatography, electrophoresis, centrifugation, and crystallization are described in Coligan et al. (2000) *Current Protocols in Protein Science*, Vol. 1, John Wiley and Sons, Inc., New York. Methods for cell-free synthesis are described in Spirin & Swartz (2008) *Cell-free Protein Synthesis*, Wiley-VCH, Weinheim, Germany. Methods for incorporation of non-native amino acids into proteins using cell-free synthesis are described in Shimizu et al., (2006) *FEBS Journal*, 273, 4133-4140.

IV. Detailed Descriptions of Embodiments

The methods provided herein can be used to generate auxotrophic *E. coli* cells that have a high growth capacity, for example, a doubling time of less than 60 minutes, e.g., 59 minutes, 58 minutes, 57 minutes, 56 minutes, 55 minutes, 54 minutes, 53 minutes, 52 minutes, 51 minutes, 50 minutes, 49 minutes, 48 minutes, 47 minutes, 46 minutes, 45 minutes, 44 minutes, 43 minutes, 42 minutes, 41 minutes, 40 minutes, or less such when cultured in chemically defined (e.g., chemically synthetic) or undefined (e.g., natural or complex) media. In some cases, the doubling time of the auxotrophic *E. coli* cells expressing a complementing plasmid is about 45 minutes. The auxotrophic strains express a complementing plasmid containing an enzyme that is able to restore the essential biosynthetic pathway that is inactivated in the cells.

The inventors have surprisingly discovered that these auxotrophic E. coli can improve and/or increase the production of biologically active proteins in a cell free synthesis system.

A. Inactivation of Genes Encoding Enzymes Responsible for Biosynthesis of Amino Acids Auxotrophic E. coli are those mutants that are unable to synthesize one or more amino acids required for its growth, proliferation or survival, or have an impaired ability to synthesize an amount of the amino acid(s) required for its growth, proliferation or survival. Accordingly, an auxotroph may be disabled or deficient for one or more target genes involved in the biosynthesis of an amino acid or in the regulation of such biosynthetic pathways.

For instance, a glutamine auxotrophic cell can have the glnA gene disrupted by deletion, partial deletion, knock out, insertion, or an introduction of one or more mutations in the gene. Similarly, a cysteine auxotroph and arginine auxotroph can have the cysE gene and the argA gene, respectively, disrupted by deletion, partial deletion, knock out, insertion, or an introduction of one or more mutations in the gene. Alternatively, the glnA, cysE or argA gene can be inactivated by antisense RNA, inhibitory RNA, or other RNA interference methods.

One approach to deleting, inserting or substituting the target gene is through the use of a nucleic acid construct comprising a knock-out of the target gene or a fragment thereof. The genome of E. coli has been completely sequenced, thereby facilitating the genetic modifications. Nucleic constructs may be produced using methods well known to those of ordinary skill in the art which can be found, for example, in standard texts such as Sambrook et al., *Molecular Cloning,* 2nd edition, Cold Spring Harbor Laboratory Press, 1989 and Ausubel et al., *Short Protocols in Molecular Biology,* 3rd ed., Wiley & Sons, 1995.

The coding sequence for one or more endogenous enzymes required for the biosynthesis of one or more amino acids can be "knocked-out" or otherwise inactivated in the chromosome of the source organism, by deletion of all or a part of the coding sequence, frame-shift insertion, dominant negative mutations, etc. The chromosomal gene can be disrupted by homologous recombination using bacteriophage recombinase systems, for example, the RecET recombinase system (Zhang et al., *Nat Genet,* 20:123-128, 1998) or the phage λ Red recombinase system (Datsenko and Wanner, *Proc Natl Acad Sci USA,* 97(12):6640-6645, 2000).

In Red-mediated recombination, the target gene is replaced with a selectable antibiotic resistance gene that is generated by PCR with primers with about 36 nucleotide extensions. After the antibiotic resistance selection, the resistance gene can be eliminated by using a plasmid expressing the FLP recombinase which actes on the FLP recognition target (FRT) sites flanking the resistance gene.

Other useful methods of gene replacement includes those described in, e.g., Hoang et al., *Gene,* 212:77-86, 1998; Arigoni et al., *Nat Biotechnol,* 16(9):851-6, 1998; Murphy, *J Bacteriol,* 180(8):2063-2071, 1998; and Court et al., *Annu Rev Genet,* 36:361-388, 2002.

The glutamine synthetase (glnA) gene of E. coli may be inactivated as described above. The genetic sequence may be accessed from public databases, e.g., NCBI GeneID: 948370 or NCBI RefSeq: NC_000913.

The serine acetyltransferase (cysE) gene of E. coli may be inactivated as described above. The genetic sequence may be accessed from public databases, e.g., NCBI GeneID: 948126 or NCBI RefSeq: NC_000913.

The N-acetylglutamate synthase (argA) gene of E. coli may be inactivated as described above. The genetic sequence may be accessed from public databases, e.g., NCBI GeneID: 947289 or NCBI RefSeq: NC_000913.

In some embodiments, the E. coli cells also have an inactivated gene encoding a protein selected from the group consisting of tryptophanase, arginine decarboxylase, L-serine deaminase and gamma-glutamylcysteine synthase. Performing cell free protein synthesis with extracts from genetically modified cells that are deficient in multiple amino acid metabolizing enzymes improves protein yield. Descriptions of such E. coli cells and extracts thereof are found in, for example, U.S. Pat. No. 7,312,049, the teachings are hereby incorporated by reference in their entirety for all purposes.

B. Testing for Auxotrophy

To screen for an auxotrophic strain, a comparison of the strain's growth rate or doubling rate in complete media and media deficient in the amino acid can be made. Typically, an amino acid auxotroph (e.g., a tryptophan auxotroph carrying a deletion in, e.g., the tryptophanase gene tnaA) can grow in media supplemented with the amino acid (e.g., tryptophan) or complex media (e.g., media containing all essential amino acids). An auxotrophic strain will not grow well or at all on media lacking the auxotrophic amino acid.

Doubling time can be determining by measuring the population density of the cells (e.g., cell density) over time. Photometric measurement of cell density at an optical density of 600 nm can be made using a standard spectrophotometer. Cell density measurements can be made at multiple time points over the time course of cell growth. Measurements of wet cell pellet weight over time can also be used to assess doubling time. For instance, a 1-liter, overnight shaking culture of E. coli with a cell density of $3\text{-}4\times10^9$/ml corresponds to a pellet wet weight of about 3 g/L.

The inventors have discovered that glnA auxotrophs, cysE auxotrophs, and argA auxotrophs, as described herein, do not grow at a doubling rate of less than 60 minutes when cultured in media deficient in glutamine, cysteine or arginine, respectively. In addition, the inventors have generated a glnA strain with a low growth rate when cultured in complex media. However, if transformed with an auxotrophic selection plasmid (an auxotrophic complementing plasmid), the auxotrophs can be cultured in incomplete, defined media (e.g., chemically defined media lacking the auxotrophic amino acid) and have a doubling time of less than 60 minutes.

C. Creation of a Complementing Plasmid

The auxotrophic strains used in the methods described herein can be transformed with a complementing plasmid that can convert the auxotrophs into high growth capacity strains. The complementing plasmids can contain an expression cassette that includes a constitutive promoter operable linked to a gene encoding an enzyme that can restores the auxotroph's ability to grow in media lacking the auxotrophic amino acid. For example, the argA auxotroph described herein can be transformed with a complementing plasmid that carries the argA gene that transcriptionally expressed under the control of a constitutive promoter.

Constitutive promoters that may be used in the present invention include native or synthetic promoters. Synthetic promoters include those described in, e.g., Jensen and Hammer, *Appl Environ Microbiol,* 64(1):82, 1998. Synthetic promoters can be generated by modifying the consensus sequences and/or spacer sequences of a native promoter.

Native promoters may be prokaryotic (including bacteriophage) promoters such as, but not limited to, lac, T3, T7, lambda Pr'P1' and trp promoters. Additional examples of constitutive promoters in bacteria include the spc ribosomal protein operon promotor $P_{spc}$, the β-lactamase gene promotor $P_{bla}$ of plasmid pBR322, the $P_L$ promoter of phage λ, the replication control promoters $P_{RNAI}$ and $P_{RNAII}$ of plasmid pBR322, the P1 and P2 promoters of the rrnB ribosomal RNA operon, the tet promoter, and the pACYC promoter.

The constitutive promoters of the complementing plasmid can have weak, medium or strong transcriptional activity. Useful examples of weak, medium and strong promoters are described in, e.g., Jensen and Hammer, *Appl Environ Microbiol,* 64(1):82, 1998. In some embodiments, a weak promoter is CP114, CP16, CP39, CP3, CP28, CP13, CP8, CP4, CP29, CP11, CP15, CP23, and the like. A medium promoter may be CP33, CP43, CP34, CP17, CP26, CP37, CP41 and the like. A strong promoter may be CP25, CP6, CP7, CP12, CP38, CP32 and CP9.

A weak promoter can have a promoter activity of <8 Miller units in *E. coli,* when cloned, for example into the multiple cloning site of a plasmid, such as pAK80. Similarly, a medium promoter can have a promoter activity of about 8-50 Miller units in *E. coli.* A strong promoter can have a promoter activity of about >50 Miller units in *E. coli.*

One of skill in the art recognizes that promoters drive transcription of RNA from adjacent DNA. A stronger promoter can drive transcription of more copies of RNA than a weaker promoter. Since RNA concentration itself can be difficult to measure, the levels of a reporter protein that are encoded by the transcribed RNA (which would then be mRNA) can be measured. The reporter protein concentration can be used to estimate the mRNA concentration. For example, a stronger promoter leads to the production of a higher level of reporter protein than a weaker promoter. A variety of reporter proteins for this purpose can be used such as GFP, or alkaline phosphatase. The term, "Miller units" refers specifically to the production of the enzyme β-galactosidase (β-gal). In this case, the promoter strength is estimated according to the amount of β-gal produced in the assay. Other factors can control the level of protein production, such as the strength of the ribosomal binding site, which determines how efficiently each mRNA is translated and the copy number of the plasmid. Analysis of the strengths of various promoters should occur in the exact same context, such that direct comparisons can be made.

The expression cassette of the complementing plasmid can be cloned into a plasmid for expression in *E. coli,* such as a multicopy plasmid. Depending on the origin of replication of the plasmid, the copy number can vary. Plasmids, such as the pUC vector, pBluescript vector, pGEM vectors, pJ201 vectors, and derivatives thereof that reach very high copy numbers (e.g., about 300-1000 or more copies) within a bacterial cell can be used. Alternatively, lower copy number plasmids, such as the pBR322 vector, pACYC vector, pSC101 vector and derivatives thereof that are presents at about 5-20 copies per bacterial cell can be used.

The complementing plasmid can also contain an antibiotic resistance gene. This gene can confer antibiotic resistance to any host cell expressing the plasmid. Non-limiting examples of an antibiotic resistance gene include genes that confer resistance to ampicillin, kanamycin, chloramphenicol, zeocin, hygromycin B, and the like.

In some embodiments, the cysE, glnA, and argA auxotrophs are transformed with a complementing plasmid expressing the cysE, glnA, and argA gene, respectively, under the control of a constitutive promoter. The complementing plasmids can also express one or more other genes of interest. For example, the plasmids can express one or more chaperones that can improve the proper folding and biological activity of proteins produced in the CFS system. Such chaperones include disulfide isomerases, e.g., DsbA, DsbB, DsbC, and DsbD, prolyl isomerases or peptidyl-prolyl cis-trans isomerase, e.g., FkpA and SlyD, and deaggregases. Detailed descriptions of useful chaperones and methods are disclosed in, for example, U.S. Appl. Publication No. 2014/0315245.

The term "disulfide isomerase," "protein disulfide isomerase," or "PDI" refers to a family of proteins comprising multiple domains, each having a typical thioredoxin (Trx) fold. The PDI molecule has two or more active sites comprising a COX motif that are the sites for isomerase activity. In vitro, PDI catalyzes the oxidative formation, reduction, or isomerization of disulfide bonds depending on the redox potential of the environment. PDIs are members of a class of folding catalysts, also called foldases. Folding catalysts assist folding by accelerating certain rate-limiting steps in the protein folding process, thereby reducing the concentration of aggregated protein folding intermediates. In addition to the isomerase function of catalyzing the formation of disulfide bonds, PDI also promotes the folding of polypeptides into their native configuration, and thus acts as a chaperone. The C-terminal region of PDI comprises the polypeptide binding region, and is believed to be responsible for the chaperone activity. The isomerase and chaperone activities of PDI are separate and independent activities, and both activities appear to be required for reactivation of reduced and denatured proteins containing disulfide bonds.

In gram-negative bacteria such as *E. coli,* disulfide bond formation, reduction and isomerization are catalyzed by the Dsb (disulfide bond formation) family of proteins, including DsbA, DsbB, DsbC, and DsbD. DsbA catalyzes the oxidative formation of disulfide bonds by transferring its active site disulfide to the target protein, which leaves DsbA in a reduced form. DsbB re-oxidizes DsbA, and passes its electrons to the respiratory chain to regenerate oxidized DsbB. DsbC catalyzes the rearrangement of disulfide bonds. DsbC is maintained in its reduced form by DsbD. DsbC is a homodimer having four thiol groups is each 23 kDa subunit monomer, two in the active site -$Cys^{98}$-Gly-Tyr-$Cys^{101}$, and the other two a $Cys^{141}$ and $Cys^{163}$. DsbC has chaperone activity that is independent from its isomerase activity. (See, e.g., Chen et al., *J. Biol. Chem.,* 1999, 274:19601-19605; and Kolag et al., *Microbial Cell Factories,* 2009, 8:9). Each monomer consists of an N-terminal dimerization domain with a cystatin fold and a C-terminal catalytic domain with a thioredoxin fold (McCarthy et al., *Nat. Struct. Biol.,* 2000, 7:196-199). Other Dsb proteins include DsbE and DsbG.

The terms "peptidyl prolyl isomerase," "peptidyl prolyl cis-trans isomerase," "prolyl isomerase," "PPI" and "PPIase" are used interchangeably, and refer to a class of chaperones known as protein folding catalysts. PPI catalyzes the conversion of trans peptidyl prolyl bonds in the amino acid proline to the cis configuration in the native or functional protein. PPIs can have different subunits or modules having different functions, for example, a module having catalytic activity and a module having chaperone or protein binding activity. Three families of PPIs are recognized: cyclophilins (whose isomerase activity is inhibited by cyclosporin A); FKBPs (FK506 binding proteins), which are inhibited by FK506 and rapamycin; and parvulins. Non-limiting examples of cyclophilins include PpiA (RotA). Non-limiting examples of FKBPs include FkpA, SlyD, and trigger factor (TF or tig). Non-limiting examples of parvulins include SurA and PpiD. Additional examples of PPIs include CypA, PpiB, Cpr1, Cpr6, and Fpr1. FkpA, SlyD, and trigger factor are related based on sequence alignments. For FkpA, the chaperone and catalytic activities reside in the N-terminal and C-terminal domains, respectively (Saul, *J. Mol. Biol.*, 2004, 335:595-608).

The term "deaggregase" refers to a protein chaperone that aids in deaggregating and/or solubilizing proteins of interest that are produced, for example, in a bacterial free translation system. Such chaperones are particularly helpful at high concentrations because their mechanism of action is stoichiometric rather than catalytic and is believed to work by stabilizing hydrophobic patches of the newly synthesized protein while the protein is folding. Examples of deaggregases include IbpA, IbpB, and Skp.

The complementing plasmids can express an RNA polymerase, for example, T7 RNA polymerase. In some embodiments, the plasmids can express more than one gene of interest. For example, the plasmids can express a chaperone as described above and T7 RNA polymerase.

In some embodiments, the complementing plasmid can express one or more translation components, e.g., aminoacyl-tRNA synthetases and suppressor tRNAs, useful for the incorporation of non-natural amino acids in a growing polypeptide chain in a cell-free protein synthesis system. The complementing plasmid can contain polynucleotides, e.g., tRNAs, and polynucleotides that encode aminoacyl-tRNA synthetases or portions thereof, such as the active site of the synthetase. Non-natural amino acids can be site-specifically integrated into proteins of interest in vitro by the addition of chemically aminoacylated suppressor tRNAs to CFS reactions that include a nucleic acid template containing with a desired nonsense mutation. The nucleic acid template can contain a nonsense codon, such as an amber, ochre, or opal stop codon, a four or more-base codon (e.g., AGGA (SEQ ID NO:1), CUAG (SEQ ID NO:2), UAGA (SEQ ID NO:3), UAGN(SEQ ID NO:4), CCCU (SEQ ID NO:5), AGGAC (SEQ ID NO:6), CCCCU (SEQ ID NO:7), CCCUC (SEQ ID NO:8), CUAGA (SEQ ID NO:9), CUACU (SEQ ID NO:10), UAGGC (SEQ ID NO:11), and the like), a rare codon, or a codon derived from natural or non-natural base pairs (e.g., iso-C:iso-G pairs, PICS:PICS pairs, 3MN:3MN pairs, and Dipic:Py pairs), such that the codon can be uniquely assigned to the non-natural amino acid of interest. The tRNA synthetase aminoacylates the suppressor tRNA, and not other tRNAs with the non-natural amino acid of interest. An exogenous tRNA/synthetase pair with an efficiency of at least 50%, e.g., at least 50%, 60%, 70%, 80%, 90% or 100% efficiency, compared to that of an endogenous tRNA/synthethase pair is generally used in the cell-free protein synthesis reaction.

The suppressor tRNA and the aminoacyl-tRNA synthetase can be derived from non-eukaryotic organisms, such as, an archaebacterium, e.g., *Methanococcus jannaschii*, *Methanobacterium thermoautotrophicum*, *Halobacterium* such as *Haloferax volcanii* and *Halobacterium* species NRC-1, *Archaeoglobus fulgidus*, *Pyrococcus furiosus*, *Pyrococcus horikoshii*, *Aeuropyrum pernix*, *Methanococcus maripaludis*, *Methanopyrus kandleri*, *Methanosarcina mazei*, *Pyrobaculum aerophilum*, *Pyrococcus abyssi*, *Sulfolobus solfataricus*, *Sulfolobus tokodaii*, *Thermoplasma acidophilum*, *Thermoplasma volcanium*, or the like, and a eubacterium, such as *Escherichia coli*, *Thermus thermophilus*, *Bacillus stearothermphilus*, or the like. Alternatively, the tRNA and the tRNA synthetase can be derived from a eukaryotic organism, such as, a plant (e.g., complex plant such as monocots or dicots), an algae, a protist, a fungus, a yeast (e.g., *Saccharomyces cerevisiae*), an animal (e.g., a mammal, an insect, an arthropod, etc.), or the like. The suppressor tRNA and the aminoacyl-tRNA synthetase can be derived from the same organism or different organisms.

The aminoacyl-tRNA synthetases have modified substrate specificity for a specific non-natural amino acid. Examples of aminoacyl-tRNA synthetases that can be used in the methods described herein, include, but are not limited to, a tyrosyl aminoacyl-tRNA synthetase (TyrRS) derived from a wild-type *E. coli* TyrRS (see, e.g., U.S. Pat. No. 7,608,423), a tyrosyl aminoacyl-tRNA synthetase (MjYRS) derived from a wild-type *M. jannaschii* TyrRS (see, e.g., U.S. Pat. No. 7,432,092; U.S. Provisional App. Nos. 61/890,028, filed Oct. 11, 2013; and 61/890,033, filed Oct. 11, 2013; and Zimmerman et al., *Bioconjugate Chem*, 2014, 25(2): 351-361), a mutant TyrRs (LWJ16) and a SS12-YyrRS (see, e.g., U.S. Pat. No. 7,045,337). The aminoacyl-tRNA synthetase of the complementing plasmid can have an amino acid sequence that is at least 80%, e.g., at least 80%, 81%, 82%, 83%, 84%, 85%, 86%, 87%, 88%, 89%, 90%, 91%, 92%, 93%, 94%, 95%, 96%, 97%, 98%, 99% or 100% identical to that of a naturally occurring tRNA synthetase.

In addition, the complementing plasmids can be used to express RNA elements. For example, the plasmids can be used to express tRNA or rRNA. In certain embodiments, the plasmids can be used to express suppressor tRNA, e.g., tRNA that recognizes a codon other than one of the 61 codons typically used by *E. coli* to encode an amino acid. Examples of useful suppressor tRNAs for the methods described herein include, but are not limited to, *Methanococcus jannaschii* tRNA$^{Tyr}_{CUA}$, *Methanococcus jannaschii* tRNA$^{Tyr}_{UCUA}$, *Methanococcus jannaschii* tRNA$^{Tyr}_{GCUA}$, *Methanococcus jannaschii* tRNA$^{Tyr}_{CCUA}$, *Methanococcus jannaschii* tRNA$^{Tyr}_{ACUA}$, *Saccharomyces cerevisiae* tRNA$^{Asp}_{CUA}$, *Saccharomyces cerevisiae* tRNA$^{Gln}_{CUA}$, *Saccharomyces cerevisiae* tRNA$^{Tyr}_{CUA}$, *Saccharomyces cerevisiae* tRNA$^{Phe}_{CUA}$, *Halobacteria* sp. NRC-1 tRNA$^{Leu}_{CUA}$, *Methanosarcina barkeri* tRNA$^{Pyl}_{CUA}$, *M. mazei* tRNA$^{Pyl}_{CUA}$, *Desulfitobacterium hafniese* tRNA$^{Pyl}_{CUA}$, *P. horikoshii* tRNA$^{Tyr}_{CUA}$, and variants thereof.

Detailed descriptions of suppressor tRNAs and aminoacyl-tRNA synthetases can be found in, for example, Wang et al., *Science*, 2001, 292: 498-500; Guo et al., *Angew Chem Int Ed Engl.*, 2009, 48(48): 9148-9151; Chatterjee et al., *Chembiochem*, 2014 May 27, doi:10.1002/cbic.201402104; Kwon et al., *J Am Chem Soc*, 2006, 128:11778-11783; Nozawa et al., *Nature*, 2009, 457(7233): 1163-1167; Liu and Schultz, *Annu Rev Biochem*, 2010, 79:413-444; Zimmerman et al., *Bioconjugate Chem*, 2014, 25(2): 351-361; U.S. Pat. Nos. 7,045,337; 7,083,971; 7,432,092; and 7,608,423; and International Application Publication Nos. WO2015054590 and WO2015054587; the disclosures are herein incorporated by reference in their entirety for all purposes.

The gene of interest can be operably linked to a promoter that initiates transcription of the gene. The promoter can be a constitutive promoter or an inducible promoter. The promoter can be prokaryotic or eukaryotic. Detailed descriptions of useful chaperones and methods of expressing chaperone are described in, e.g., International Appl. Publication No. WO2014172631, the contents of herein incorporated by reference in their entirety for all purposes.

D. Transformation of Auxotrophic Strain with Plasmid with an Auxotrophic Selection Marker The complementing plasmids can be transformed into the auxotrophs to generate high growth capacity bacterial strains. Firstly, the auxotrophs described herein can be made into electrocompetent or chemically competent cells that can take up the complementing plasmid. Methods for preparing electrocompetent and chemically competent cells are described in, e.g., Ausubel, F. M., et al., *Current Protocols in Molecular Biology*, John Wiley & Sons, New York (2012). For example, electrocompetent cells can be made from an auxotroph culture in log phase by repeatedly resuspending the pelleted cells in ice-cold 10%-15% glycerol. Chemically competent auxotrophs can be made by treating the cells with ice cold $CaCl_2$. Transforming plasmids into bacterial cells is well known to those of skill in the art. Such methods include, for example, electroporation or heat shock (see, Sambrook et al., *Molecular Cloning*, 2nd edition, Cold Spring Harbor Laboratory Press, (1989)).

To select auxotrophs that express the complementing plasmid, the transformed cells can be cultured under antibiotic selection when the plasmid contains an antibiotic resistance gene or under auxotrophic selection. For instance, the transformed auxotroph can be grown in media containing an antibiotic corresponding to the antibiotic resistance gene expressed by the plasmid. Those cells that survive and grow in the antibiotic supplemented media carry the complementing plasmid. Alternatively, the transformed auxotroph can be cultured in media lacking the auxotrophic amino acid. Cells that survive and grow in media harbor the complementing plasmid.

The complemented auxotrophic cells described herein have high growth capacity and have a doubling time of less than 60 minutes, e.g., about 45 minutes. These cells can be grown to a high density in complete media or media lacking the auxotrophic amino acid. The media lacking the auxotrophic amino acid can be chemically defined media. These cells can be used in cell-free protein synthesis systems. In particular, a bacterial extract can be produced from these cells and used to produce proteins of interest.

E. Production of Biologically Active Proteins of Interest Using a Cell Free Synthesis System Biologically active proteins of interest can be synthesized, properly folded and/or assembled using a cell-free synthesis (CFS) system such as an *Escherichia coli*-based open cell-free (OCFS) system. In such a system, a cell extract from *E. coli* cells, such as the auxotrophs described herein, can be harvested in exponential growth phase and serves as a source of ribosomes and other cellular factors required for in vitro protein synthesis. The cell extract can be mixed with template DNA (such as plasmid or linear DNA fragments), amino acids (including native or non-native amino acids), nucleotides, T7 RNA polymerase, and an energy source. Optionally, disulfide isomerase chaperones is also added to aid in the formation of disulfide bonds. CFS systems have been used to generate various proteins including growth factors (Zawada et al., *Biotechnol Bioeng*, 108:1570-1578 (2011)), full-length antibodies and antibody fragments (Yin et al., mAbs, 4(2):217-225 (2012)) and antibody-drug conjugates (Zimmerman et al., *Bioconjug Chem*, 25(2):351-61 (2014)).

A bacterial extract of an auxotrophic strain can be generated as follows. The bacteria of choice may be grown to log phase in any of a number of growth media and under growth conditions that are well known in the art and easily optimized by a practitioner for growth of the particular bacteria. For example, a natural environment for synthesis utilizes cell lysates derived from bacterial cells grown in medium containing glucose and phosphate, where the glucose is present at a concentration of at least about 0.25% (weight/volume), more usually at least about 1%; and usually not more than about 4%, more usually not more than about 2%. Examples of media that can be used include 2YTPG medium and DM 80-80 media. One of skill in the art will appreciate that many culture media can be adapted for this purpose, as there are many published media suitable for the growth of bacteria such as *E. coli*, using both defined and undefined sources of nutrients. It has been shown that high density cell cultures with rapid growth rates (e.g., doubling time of about <60 minutes) generate a high concentrations of ribosomes which improves the production of proteins in CFS systems (Zawada and Swartz, *Biotechnol Bioeng*, 94(4):618-24 (2006)). After fermentation the cells can be harvested and lysed by suspending the cell pellet in a suitable cell suspension buffer, and disrupting the suspended cells by sonication, breaking the suspended cells in a French press, continuous flow high pressure homogenization, or any other method known in the art useful for efficient cell lysis. The cell extract may be centrifuged or filtered to remove large DNA fragments and cell debris. In some embodiments, the bacterial extract is dried prior to use in the protein synthesis reaction mix. A detailed description of bacteria fermentation and extract preparation are found in, for example, Zawada et al., *Biotechnol Bioeng*, 108:1570-1578 (2011) and Zawada, J F, *Methods Mol Biol*, 805:31-41 (2012), the teachings are hereby incorporated by reference in their entirety for all purposes.

The bacterial strain used to make the cell extract may have reduced nuclease and/or phosphatase activity which increases cell free synthesis efficiency. For example, the bacterial strain used to make the cell free extract can have mutations in the genes encoding the nucleases RNase E and RNase A. The strain may also have mutations to stabilize components of the cell synthesis reaction such as deletions in genes such as tnaA, speA, sdaA or gshA, which prevent degradation of the amino acids tryptophan, arginine, serine and cysteine, respectively, in a cell-free synthesis reaction. Additionally, the strain may have mutations to stabilize the protein products of cell-free synthesis such as knockouts in the proteases ompT or lonP.

In a generic CFS reaction, a gene encoding a protein of interest is expressed in a transcription buffer, resulting in mRNA that is translated into the protein of interest in a CFPS extract and a translation buffer. The transcription buffer, cell-free extract and translation buffer can be added separately, or two or more of these solutions can be combined before their addition, or added contemporaneously.

To synthesize a protein of interest in vitro, a CFS extract at some point comprises a mRNA molecule that encodes the protein of interest. In some CFS systems, mRNA is added exogenously after being purified from natural sources or prepared synthetically in vitro from cloned DNA using RNA polymerases such as RNA polymerase II, SP6 RNA polymerase, T3 RNA polymerase, T7 RNA polymerase, RNA polymerase III and/or phage derived RNA polymerases. In other systems, the mRNA is produced in vitro from a template DNA; both transcription and translation occur in this type of CFS reaction. In some embodiments, the transcription and translation systems are coupled or comprise complementary transcription and translation systems, which carry out the synthesis of both RNA and protein in the same reaction. In such in vitro transcription and translation systems, the CFS extracts contain all the components (exogenous or endogenous) necessary both for transcription (to produce mRNA) and for translation (to synthesize protein) in a single system.

A CFS reaction mixture can contain the following components: a template nucleic acid, such as DNA, that comprises a gene of interest operably linked to at least one promoter and, optionally, one or more other regulatory sequences (e.g., a cloning or expression vector containing the gene of interest) or a PCR fragment; an RNA polymerase that recognizes the promoter(s) to which the gene of interest is operably linked (e.g. T7 RNA polymerase) and, optionally, one or more transcription factors directed to an optional regulatory sequence to which the template nucleic acid is operably linked; ribonucleotide triphosphates (rNTPs); optionally, other transcription factors and co-factors therefor; ribosomes; transfer RNA (tRNA); other or optional translation factors (e.g., translation initiation, elongation and termination factors) and co-factors therefore; one or more energy sources, (e.g., ATP, GTP); optionally, one or more energy regenerating components (e.g., PEP/pyruvate kinase, AP/acetate kinase or creatine phosphate/creatine kinase); optionally factors that enhance yield and/or efficiency (e.g., nucleases, nuclease inhibitors, protein stabilizers, chaperones) and co-factors therefore; and; optionally, solubilizing agents. The reaction mix can also include amino acids and other materials specifically required for protein synthesis, including salts (e.g., potassium, magnesium, ammonium, and manganese salts of acetic acid, glutamic acid, or sulfuric acids), polymeric compounds (e.g., polyethylene glycol, dextran, diethyl aminoethyl dextran, quaternary aminoethyl and aminoethyl dextran, etc.), cyclic AMP, inhibitors of protein or nucleic acid degrading enzymes, inhibitors or regulators of protein synthesis, oxidation/reduction adjuster (e.g., DTT, ascorbic acid, glutathione, and/or their oxides), non-denaturing surfactants (e.g., Triton X-100), buffer components, spermine, spermidine, putrescine, etc. Components of CFS reactions are discussed in more detail in U.S. Pat. Nos. 7,338,789; 7,351,563, and 8,715,958 and U.S. App. Pub. No. 2010/0184135, the disclosures of each are incorporated by reference in their entirety for all purposes.

Depending on the specific enzymes present in the extract, for example, one or more of the many known nuclease, polymerase or phosphatase inhibitors can be selected and advantageously used to improve synthesis efficiency.

Protein and nucleic acid synthesis typically requires an energy source. Energy is required for initiation of transcription to produce mRNA (e.g., when a DNA template is used and for initiation of translation high energy phosphate for example in the form of GTP is used). Each subsequent step of one codon by the ribosome (three nucleotides; one amino acid) requires hydrolysis of an additional GTP to GDP. ATP is also typically required. For an amino acid to be polymerized during protein synthesis, it must first be activated. Significant quantities of energy from high energy phosphate bonds are thus required for protein and/or nucleic acid synthesis to proceed.

An energy source is a chemical substrate that can be enzymatically processed to provide energy to achieve desired chemical reactions. Energy sources that allow release of energy for synthesis by cleavage of high-energy phosphate bonds such as those found in nucleoside triphosphates, e.g., ATP, are commonly used. Any source convertible to high energy phosphate bonds is especially suitable. ATP, GTP, and other triphosphates can normally be considered as equivalent energy sources for supporting protein synthesis.

To provide energy for the synthesis reaction, the system can include added energy sources, such as glucose, pyruvate, phosphoenolpyruvate (PEP), carbamoyl phosphate, acetyl phosphate, creatine phosphate, phosphopyruvate, glyceraldehyde-3-phosphate, 3-Phosphoglycerate and glucose-6-phosphate, that can generate or regenerate high-energy triphosphate compounds such as ATP, GTP, other NTPs, etc.

When sufficient energy is not initially present in the synthesis system, an additional source of energy is preferably supplemented. Energy sources can also be added or supplemented during the in vitro synthesis reaction.

In some embodiments, proteins containing a non-natural amino acid (nnAA) may be synthesized. In such embodiments, the reaction mix may comprise the non-natural amino acid, a tRNA orthogonal to the 20 naturally occurring amino acids, and a tRNA synthetase that can link the nnAA with the orthogonal tRNA. See, e.g., U.S. Pat. No. 8,715,958. Alternatively, the reaction mix may contain a nnAA conjugated to a tRNA for which the naturally occurring tRNA synthetase has been depleted. See, e.g., U.S. App. Publ. Nos. 2010/0184134, 2010/0184135, and 2014/060058 and International Appl. Publ. Nos. WO2015054587, WO2015054590, and WO2015054658. Various kinds of unnatural amino acids, including without limitation detectably labeled amino acids, can be added to CFS reactions and efficiently incorporated into proteins for specific purposes. See, for example, Albayrak, C. and Swartz, J R., *Biochem. Biophys Res. Commun.*, 431(2):291-5; Yang W C et al., *Biotechnol. Prog.* (2012), 28(2):413-20; Kuechenreuther et al., *PLoS One*, (2012), 7(9):e45850; and Swartz J R., *AIChE Journal*, 58(1):5-13.

In some instances, the cell-free synthesis reaction does not require the addition of commonly secondary energy sources, yet uses co-activation of oxidative phosphorylation and protein synthesis. In some instances, CFS is performed in a reaction such as the Cytomim™ (cytoplasm mimic) system. The Cytomim™ system is defined as a reaction condition performed in the absence of polyethylene glycol with optimized magnesium concentration. This system does not accumulate phosphate, which is known to inhibit protein synthesis. Detailed descriptions of the Cytomim™ system are found in, for example, U.S. Pat. No. 7,338,789, the contents are hereby incorporated in their entirety for all purposes.

The presence of an active oxidative phosphorylation pathway can be tested using inhibitors that specifically inhibit the steps in the pathway, such as electron transport chain inhibitors. Examples of inhibitors of the oxidative phosphorylation pathway include toxins such as cyanide, carbon monoxide, azide, carbonyl cyanide m-chlorophenyl hydrazone (CCCP), and 2,4-dinitrophenol, antibiotics such as oligomycin, pesticides such as rotenone, and competitive inhibitors of succinate dehydrogenase such as malonate and oxaloacetate.

In some embodiments, the cell-free protein synthesis reaction is performed using the Cytomim system comprising NTPs, *E. coli* tRNA, amino acids, $Mg^{2+}$ acetate, $Mg^{2+}$ glutamate, $K^+$ acetate, $K^+$ glutamate, folinic acid, Tris pH 8.2, DTT, pyruvate kinase, T7 RNA polymerase, disulfide isomerase, sodium pyruvate, NAD, CoA, $Na^+$ oxalate, putrescine, spermidine, and S30 extract. In some embodiments, the energy substrate for the Cytomim system is pyruvate, glutamic acid, and/or glucose. In some embodiments of the system, the nucleoside triphosphates (NTPs) are replaced with nucleoside monophosphates (NMPs).

The cell extract can be treated with iodoacetamide in order to inactivate enzymes that can reduce disulfide bonds and impair proper protein folding. As further described herein, the cell extract can also be treated with a prokaryotic disulfide bond isomerase, such as, not limited to, *E. coli* DsbC and PDI. The cell extract can be treated with DsbC, FkpA and peptidyl peolyl isomerase. Exogenous chaperone proteins can be expressed by the bacteria strain of the cell extract. Glutathione disulfide (GSSG) and glutathione (GSH) can also be added to the extract at a ratio that promotes proper protein folding and prevents the formation of aberrant protein disulfides.

In some embodiments, the CFS reaction includes inverted membrane vesicles to perform oxidative phosphorylation. These vesicles can be formed during the high pressure homogenization step of the preparation of cell extract process, as described herein, and remain in the extract used in the reaction mix.

The cell free synthesis reaction conditions may be performed as batch, continuous flow, or semi-continuous flow, as known in the art. The reaction conditions are linearly scalable, for example, the 0.3 L scale in a 0.5 L stirred tank reactor, to the 4 L scale in a 10 L fermentor, and to the 100 L scale in a 200 L fermentor.

The development of a continuous flow in vitro protein synthesis system by Spirin et al. (1988) Science 242:1162-1164 proved that the reaction could be extended up to several hours. Since then, numerous groups have reproduced and improved this system (see, e.g., Kigawa et al. (1991) *J. Biochem.* 110:166-168; Endo et al. (1992) J. Biotechnol. 25:221-230). Kim and Choi (*Biotechnol. Prog.* 12: 645-649, 1996) have reported that the merits of batch and continuous flow systems can be combined by adopting a "semicontinuous operation" using a simple dialysis membrane reactor. They were able to reproduce the extended reaction period of the continuous flow system while maintaining the initial rate of a conventional batch system. However, both the continuous and semi-continuous approaches require quantities of expensive reagents, which must be increased by a significantly greater factor than the increase in product yield.

Several improvements have been made in the conventional batch system (Kim et al. (1996) *Eur. J. Biochem.* 239: 881-886; Kuldlicki et al. (1992) *Anal. Biochem.* 206:389-393; Kawarasaki et al. (1995) *Anal. Biochem.* 226: 320-324). Although the semicontinuous system maintains the initial rate of protein synthesis over extended periods, the conventional batch system still offers several advantages, e.g. convenience of operation, easy scale-up, lower reagent costs and excellent reproducibility. Also, the batch system can be readily conducted in multiplexed formats to express various genetic materials simultaneously.

The protein synthesis reactions described herein can utilize a large scale reactor, small scale, or may be multiplexed to perform a plurality of simultaneous syntheses. Continuous reactions can use a feed mechanism to introduce a flow of reagents, and may isolate the end-product as part of the process. Batch systems are also of interest, where additional reagents may be introduced to prolong the period of time for active synthesis. A reactor can be run in any mode such as batch, extended batch, semi-batch, semi-continuous, fed-batch and continuous, and which will be selected in accordance with the application purpose.

V. Examples

The following examples are provided by way of illustration only and not by way of limitation. Those of skill will readily recognize a variety of noncritical parameters which could be changed or modified to yield essentially similar results.

Example 1. Producing Auxotrophic Strains by Inactivating glnA, cysE or argA

This example illustrates a method for generating glnA, cysE or argA auxotrophic *E. coli* strains. The method utilizes the λ Red recombinase system for homologous recombination (see, Datsenko and Wanner, *Proc Natl Acad Sci USA*, 97(12):6640-6645, 2000). Briefly, the target gene (e.g., the glnA, cysE or argA gene) was replaced by a selectable marker that was flanked by FRT sites, and then the selectable marker was excised using FLP recombinase. This two-step process efficiently and effectively inactivated the target gene.

Figure 1B:
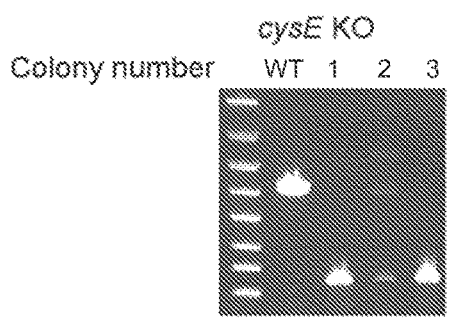
Figure 1C:
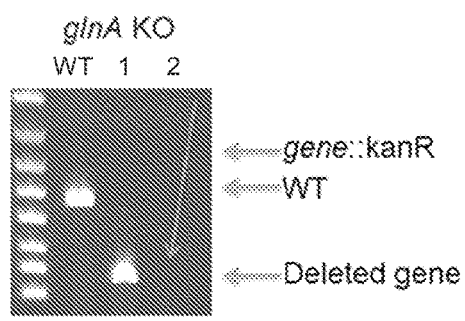

A targeting cassette was amplified by PCR to contain 36- to 50-nucleotide long extensions that are homologous to regions adjacent to the target gene and are located at both the 5' and 3' ends of a FRT-flanked selectable marker (e.g., a kanamycin-resistance gene ($Kan^R$)). The targeting cassette was introduced by electroporation into *E. coli* cells carrying the Red gene disruption system. Kanamycin resistant colonies were identified. These colonies were screened to determine whether they were auxotrophic, indicating that the Kan cassette had integrated into the correct location. PCR analysis was performed to verify integration of the $Kan^R$ gene into the target gene. The selectable marker was eliminated by expressing the FLP recombinase in the targeted cells. As expected, this approach left a gene knockout scar at the site of FRT-FLP recombination. Colony PCR of the genomic regions of the target genes confirmed successful gene inactivation and removal of the selection marker in the auxotrophs (FIG. 1). Further, each auxotrophic strain failed to grow on minimal media lacking the auxotrophic amino acid. Specifically, the glnA auxotrophs did not grow on media without glutamine. The cysE auxotrophs did not grow in the absence of cysteine and the argA auxotrophs did not grow on media lacking arginine. This example describes the generation of auxotrophs using the λ Red recombinase system.

Example 2. Generating Complementing Plasmids (e.g., Auxotrophic Selection Plasmids)

This example demonstrates a method for producing complementing plasmids (e.g., auxotrophic selection plasmids). The plasmids can be introduced into auxotrophic cells to generate complemented auxotrophic cells that can grow in media lacking the auxotrophic amino acid. The plasmids can be used to apply auxotrophic selection pressure on the complemented cells. Furthermore, the resulting cells have high growth capacity.

The auxotrophic selection plasmids were based on either a high copy number plasmid (e.g., pUC) or a medium (lower) copy number plasmid (e.g., pACYC). The plasmids contained either a strong, medium, or weak promoter operably linked to an auxotrophic gene (e.g., the cysE, glnA, or argA gene). The promoters were selected based on the study described in Jensen and Hammer (*Appl Environ Mirobiol*, 64(1):82-87, 1998). The plasmids also included a chaperone (e.g., DsbC and FkpA) which aids in disulfide bond formation or quaternary protein assembly during cell free protein synthesis.

Figure 2A:
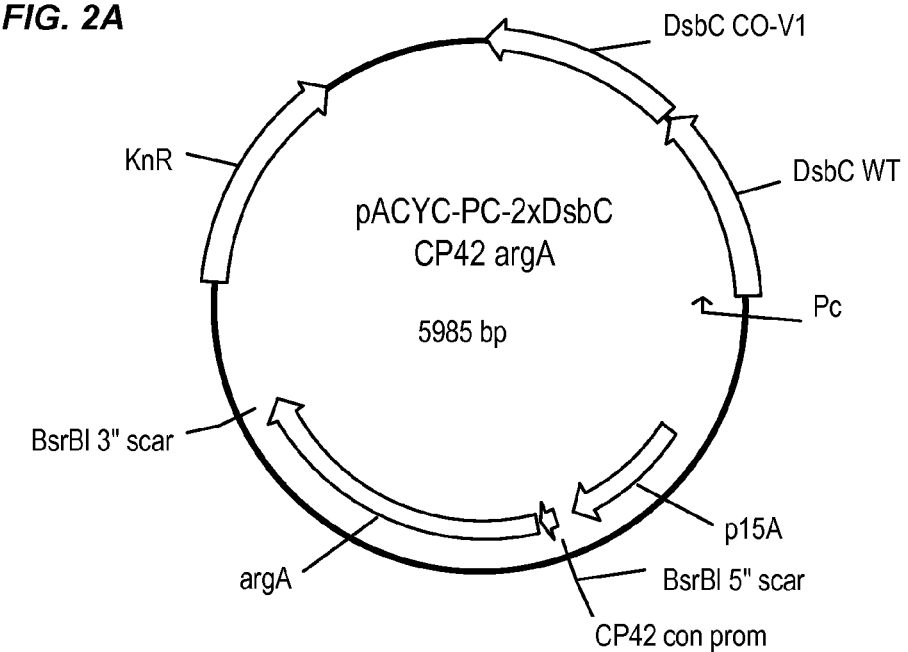
FIGS. 2A-B show representative auxotrophic selection plasmids; pACYC-Pc-2xDsbc CP42 argA in FIG. 2A and pJ201 Mj tRNA pAzF CP3 glnA in FIG. 2B.

The medium copy plasmids had an ACYC origin of replication. This plasmid system has been used for the expression of DsbC, FkpA and both FkpA and tRNA for non-natural amino acid incorporation. An example of a medium copy, complementing argA plasmid is shown in FIG. 2A. To clone the complementing plasmid, the pACYC-Pc plasmid was digested at a unique restriction site, such as BsrBI or NheI. The auxotrophic gene (glnA, cysE, or argA) was amplified from the wildtype *E. coli* strain SBJY001 using PCR primers that had sequence homology to the 5' and 3' regions flanking the unique pACYC-Pc restriction site. These PCR primers also introduced a strong, medium or weak constitutive promoter (e.g., CP9, CP42 or CP3 promoter) upstream of the auxotrophic gene to control for the transcription of the gene. The PCR amplicon fragment was then cloned into pACYC-Pc using directional cloning, e.g., choo-choo cloning. Each auxotrophic selection plasmid was verified by sequence analysis. In some instances, the pACYC vector was used for expression of only a tRNA for non-natural amino acid incorporation.

A similar cloning strategy was employed using pACYC-Pc based bicistronic plasmids, such as pACYC-Pc-2×DsbC which contains the bacterial gene DsbC behind a constitutive promoter and pACYC-Pc-2×FkpA which contains the bacterial gene FkpA behind a constitutive promoter. For example, the pACYC-Pc-2×DsbC CP42 argA plasmid was cloned to include the argA gene under the control of the CP42 promoter, as well as two DsbC coding sequences under the control of another constitutive promoter in the pACYC-Pc vector backbone.

Figure 2B:
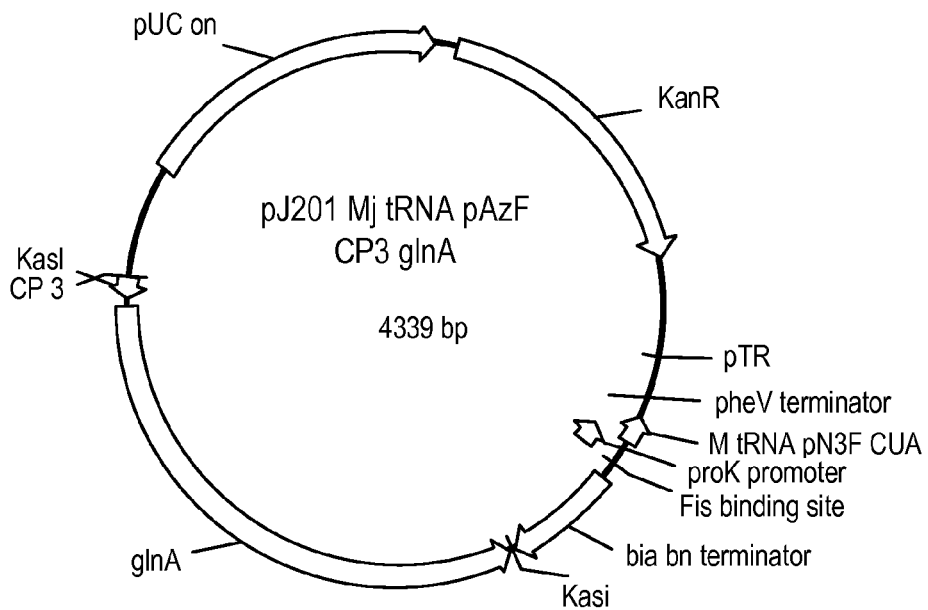

The high copy plasmids were based on the pUC origin of replication. The plasmid backbone used was pJ201. This plasmid has been used to drive high level production of tRNA for non-natural amino acid incorporation. An example of a high copy, complementing glnA plasmid is shown in FIG. 2B. To clone the auxotrophic gene into this plasmid, the plasmid backbone was digested at the unique restriction site KasI. The auxotrophic gene was amplified from *E. coli* chromosomal DNA by colony PCR using primers with homology to the plasmid backbone. The PCR primers also contained a strong, medium or weak constitutive promoter (e.g., CP9, CP42 or CP3 promoter) for the auxotrophic gene. The PCR amplicon fragment was then cloned into pJ201 with directional cloning, e.g., choo-choo cloning. Each auxotrophic selection plasmid was verified by sequence analysis.

The complementing plasmids described herein included a kanamycin selection marker. This provided added versatility to the system and allowed the plasmid to be maintained in the transformed cells either under antibiotic selection or auxotrophic selection. Therefore, standard media for molecular biology manipulations such as transformations and strain propagation were used to maintain the plasmid in the transformed strains.

Example 3. Transformation of *E. coli*

This example provides an exemplary method of transforming a complementing plasmid into auxotrophic cells to generate high capacity growth strains.

To prepare electrocompetent cells from the auxotrophic strains, an overnight culture of 2×YT broth was inoculated with cells from a single, freshly grown colony. The following morning, the culture was diluted 1:50 into fresh 2YT and grown to an $OD_{600}$ of 0.65. The culture was then quick-chilled on wet ice, poured into sterile centrifuge bottles and centrifuged at 5000×g. The cell pellet was resuspended in a culture volume of sterile, ice-cold 15% glycerol. After two more cycles of centrifugation and resuspension in glycerol, the pellet was resuspended in ice-cold 15% glycerol to an $OD_{600}$ of around 200, aliquotted into microcentrifuge tubes and then frozen and stored at −80° C.

To transform the electrocompetent auxotrophic cells, an aliquot thawed on ice was mixed with 100 ng of the complementing auxotrophic selection plasmid. The mixture was pipetted into a chilled electroporation cuvette and pulsed in a BioRad™ Gene Pulser Xcell electroporator according to the manufacturer's instructions for bacterial transformation. The transformed cells were recovered in 100 μl SOC for 1 hour at 37° C. in a rotating shaker. 25 μl of this recovery was plated onto an LB kanamycin plate which was then incubated at 37° overnight.

The argA auxotrophs were transformed with either the pACYC-Pc-2×DsbC CP9 argA plasmid or pACYC-Pc-2×DsbC CP42 argA plasmid. The glnA auxotrophs were transformed with either the pACYC-Pc-2×DsbC CP42 glnA plasmid or pACYC-Pc-2×DsbC CP9 plasmid. The cysE auxotrophs were transformed with either the pACYC-Pc-2×DsbC CP42 cysE plasmid or pACYC-Pc-2×DsbC CP9 cysE plasmid.

The transformed cells were streaked out onto minimal media plates to verify the functional complementation of the genetic lesion on the chromosome. All the transformed cells grew on media lacking the auxotrophic amino acid.

Electrocompetent cells produced from the auxotrophic strains had transformation efficiencies of around $5 \times 10^9$ colonies, and corresponding chemically competent auxotrophic cells had at least 1000 colonies. The pACYC-based and p15A-based plasmids were present in around 15 copies per cell, and pUC based plasmids were present at about 300 copies per cell. These copy numbers are independent of the other genes contained on the plasmid. The titers of the other gene products in these vectors such as non-natural tRNA, DsbC, or FkpA were unchanged between antibiotic selection and auxotrophic selection. The intracellular concentrations of these gene products were also copy-number dependent. The results indicate that the copy number for the complementing plasmids remained unchanged compared to their parental plasmids.

Example 4. Culturing Transformants in Amino Acid Deficient Media

To apply auxotrophic selection pressure to the transformed auxotrophic stains, the cells can be grown in essentially any media that lacks the auxotrophic amino acid. For routine molecular biology applications, MOPS minimal M9 media supplemented with glucose, containing 9 essential salts and an energy and carbon source in the form of glucose was used. For extract fermentations, DM 80-80 media which contains a richer defined mixture including vitamins and up to 13 amino acids was used to ensure high levels of growth. Antibiotic selection and auxotrophic selection were used to test whether the transformed auxotrophic strains retained the complementing plasmid.

To measure stability of the strains under auxotrophic selection, the complemented cells were grown up overnight in LB supplemented with kanamycin. The next day, the cells were diluted into sterile defined media (e.g., DM 80-80 media) lacking the auxotrophic amino acid at a 1:40 dilution. For the fermentation the next day, the cells were directly diluted into DM 80-80 media for auxotrophic selection, and then grown overnight. The next morning the cultures were diluted $1:1 \times 10^6$ and then plated on selective LB agar plates with kanamycin and non-selective LB agar plates. To determine the percentage of colonies that retained the complementing plasmid, the number of colonies on the selective plates was divided by the number of colonies on the non-selective plates.

Figure 3:
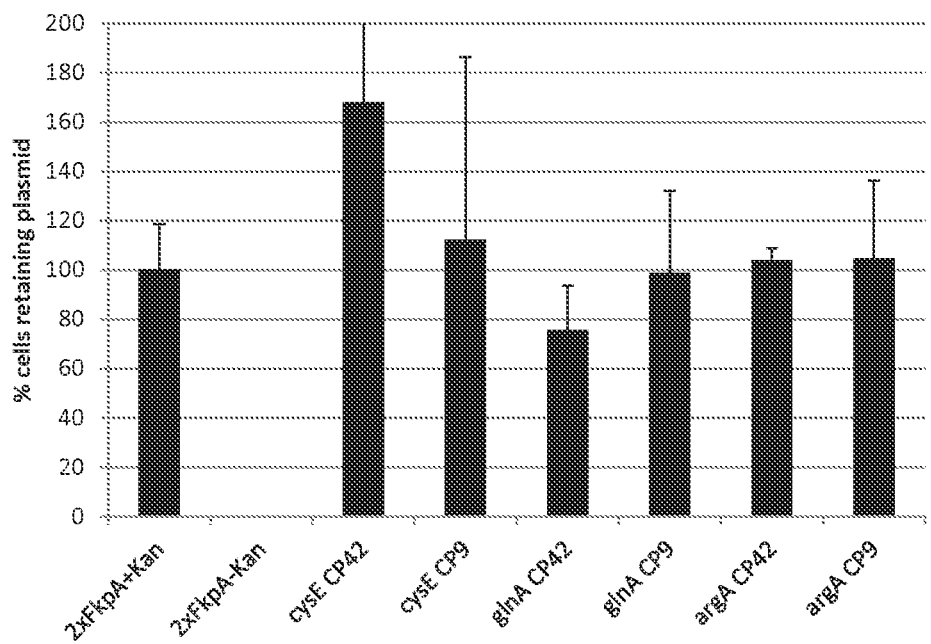
FIG. 3 shows plasmid maintenance in the DM 80-80 media without the auxotrophic amino acids. The cells were tested after growing overnight in DM 80-80 media without amino acids at 37° C.

The data shows that that auxotrophic selection of plasmid pACYC-Pc-2×FkpA was as effective as antibiotic selection in defined media lacking the auxotrophic amino acids (FIG. 3). In the DM 80-80 media without the amino acids, plasmids lacking an auxotrophic selection marker in WT cells were not maintained in the absence of antibiotic selection. However, both antibiotic selection and auxotrophic selection were sufficient to maintain the complementing plasmids in almost 100% of cells in these media. This high level of plasmid maintenance was observed for all three amino acid auxotrophic systems investigated.

To measure the growth rates of complemented cells undergoing auxotrophic selection pressure, the cells were grown overnight in DM 80-80 media lacking kanamycin at 37° C. with 225 RPM agitation. In the morning each culture was diluted 1:40 into fresh DM 80-80 media supplemented with antifoam in a baffled flask and cultured at 37° C. with 225 RPM agitation. Kanamycin was only added to the control culture. The turbidity of these cells was monitored until the cultures reached an $OD_{600}$ over 1.

Figure 4A:
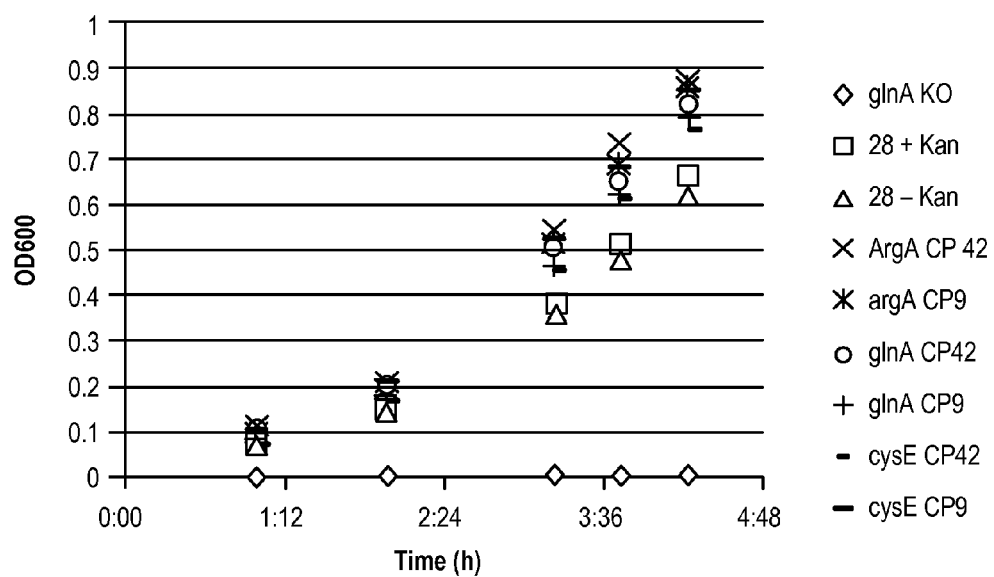
FIGS. 4A-B show the growth of the transformed strains using auxotrophic selection.
Figure 4B:
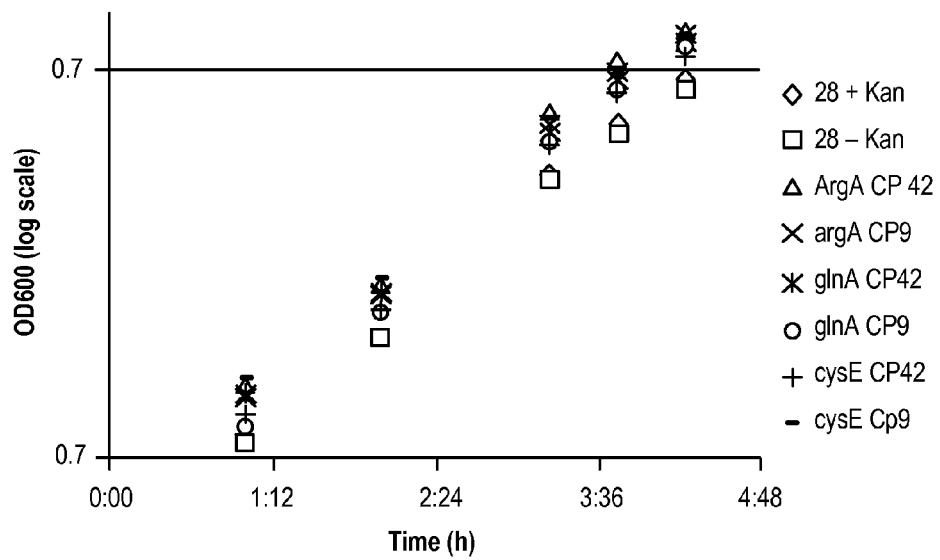

The control auxotrophs that do not carry the complementing plasmid were unable to grow in media lacking the auxotrophic amino acid. The growth rate of the complemented strains (e.g., argA CP9, argA CP42, cysE CP9, cysE CP42, glnA CP9, and glnA CP42) was indistinguishable from wild-type cells utilizing antibiotic selection (e.g., 28+Kan). See, FIGS. 4A-B. In FIG. 4B the growth rate is proportional to the slope of the line through each time point of the log scale graph. The data shows that each of the complementing strains had a similar growth rate. In particular, the doubling time for each strain was about 56 to about 60 minutes. This example shows that the complemented auxotrophic strains have high growth capacity.

Example 5. Culturing Auxotrophs and Transformants in Complete Media

This example illustrates that auxotrophic selection pressure can be applied to a complemented strain in the presence of the auxotrophic amino acid. In particular, this example shows that while the glnA auxotroph has an extreme growth defect, the glnA complemented strain can grow robustly in this media.

All three auxotrophs were grown alongside the glnA auxotroph transformed with either pACYC-2×FkpA-glnA CP9 or pACYC-2×FkpA-glnA CP42. These strains were grown overnight in terrific broth (TB) at 37° C. with 225 RPM agitation. TB contains 1.2% w/v tryptone which is a source of all amino acids. The media for the transformed strains was supplemented with kanamycin to ensure that cells retained the plasmids. The next day, each culture was diluted 1:50 into fresh TB. The OD of each sample was measured until $OD_{600}>1.0$.

Figure 5:
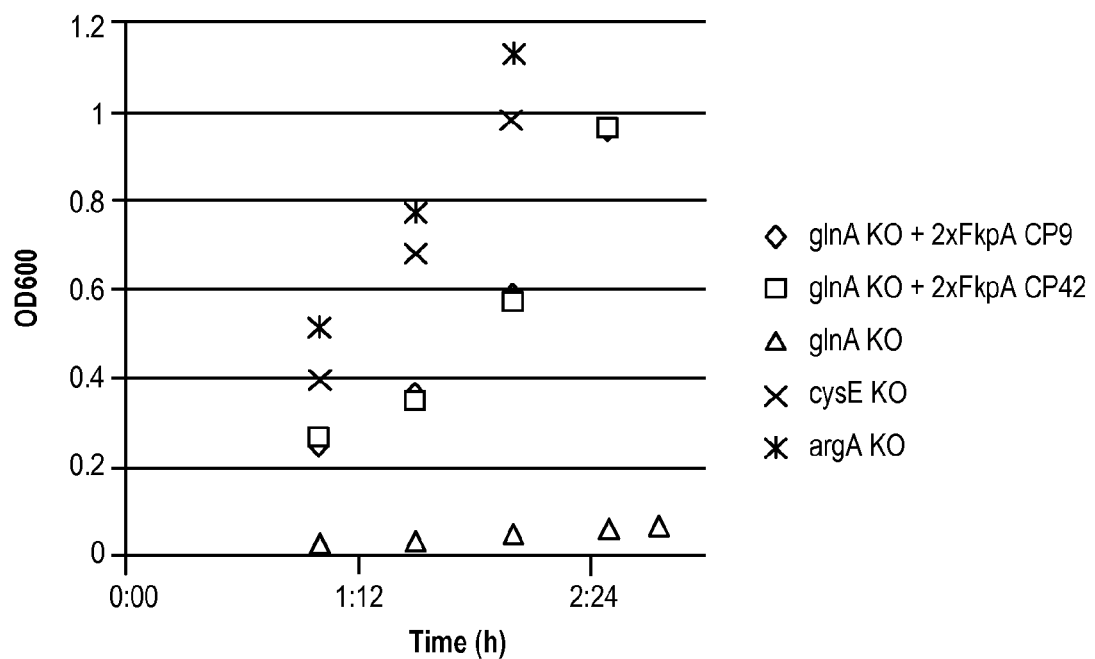
FIG. 5 shows the growth of the auxotrophic strain in complex media that contains all amino acids.

The glnA auxotroph showed a substantial growth defect that was not observed with the cysE or argA mutants (FIG. 5). This defect was corrected by transformation with a glnA expressing plasmid such as pACYC-2×FkpA-glnA CP9 or pACYC-2×FkpA-glnA CP42. Although the growth rate for the two transformed strains was slower than for the argA or cysE mutants, this is likely due to the extra metabolic burden of plasmid replication and expression of the protein FkpA. The increase in growth rate upon restoration of the function glutamine biosynthesis pathway shows that selective pressure was applied to the cell to maintain the plasmid, even in the presence of the auxotrophic amino acid. glnA auxotrophs that lose the complementing plasmid grow more slowly and are overgrown by cells that still contain the plasmid.

Example 6. CFS with Transformants Produce High Protein Yields

The auxotrophic strain SBDG098 with a deletion lesion in glnA was transformed with the complementary auxotrophic pACYC-Pc0-2×FkpA CP42 glnA plasmid. The cells were grown to high density in DM 80-80 media as previously described (Zawada et al., *Biotechnol Bioeng*, 2011, 108(7): 1570-1578). The cells were pelleted at 12,000×g for 45 minutes and then washed in S30 buffer two times. These cells were then converted into cell-free extract following the protocol from (Zawada, supra). Cell-free trastuzumab was produced in an overnight cell free reaction using the OCFS conditions described previously for GM-CSF (Zawada, supra) with the following modifications: 13 µM DsbC was added to each reaction, and the total plasmid concentrations were 10 µg/ml with a 3:1 ratio of the trastuzumab heavy chain plasmid to light chain plasmid. The amount of properly assembled IgG was quantified based on $^{14}$C-Leucine incorporation into the protein which was subsequently measured with autoradiography after separation on a non-reducing PAGE gel.

Figure 6:
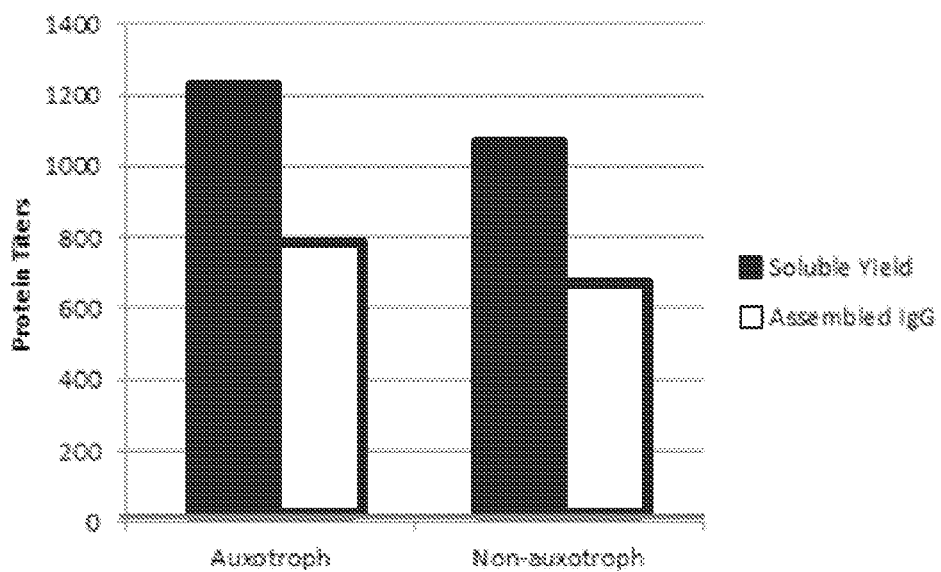
FIG. 6 shows the protein titers from the open cell free protein synthesis reactions using bacterial extracts produced from auxotrophic and non-auxotrophic selection for the plasmid pACYC-Pc-2x-FkpA. The titers were calculated from the incorporation of $^{14}C$-leucine into full-length IgG produced in the overnight reaction.

The assembled IgG titers produced using extract prepared from the auxotrophic strain are similar to the equivalent non-auxotrophic strain. In FIG. 6, both the soluble protein and properly assembled IgG titers for the auxotrophic strain are slightly higher than for the regular strain employing antibiotic selection, reaching an IgG production level of nearly 800 mg/ml in an overnight reaction.

Figure 7:
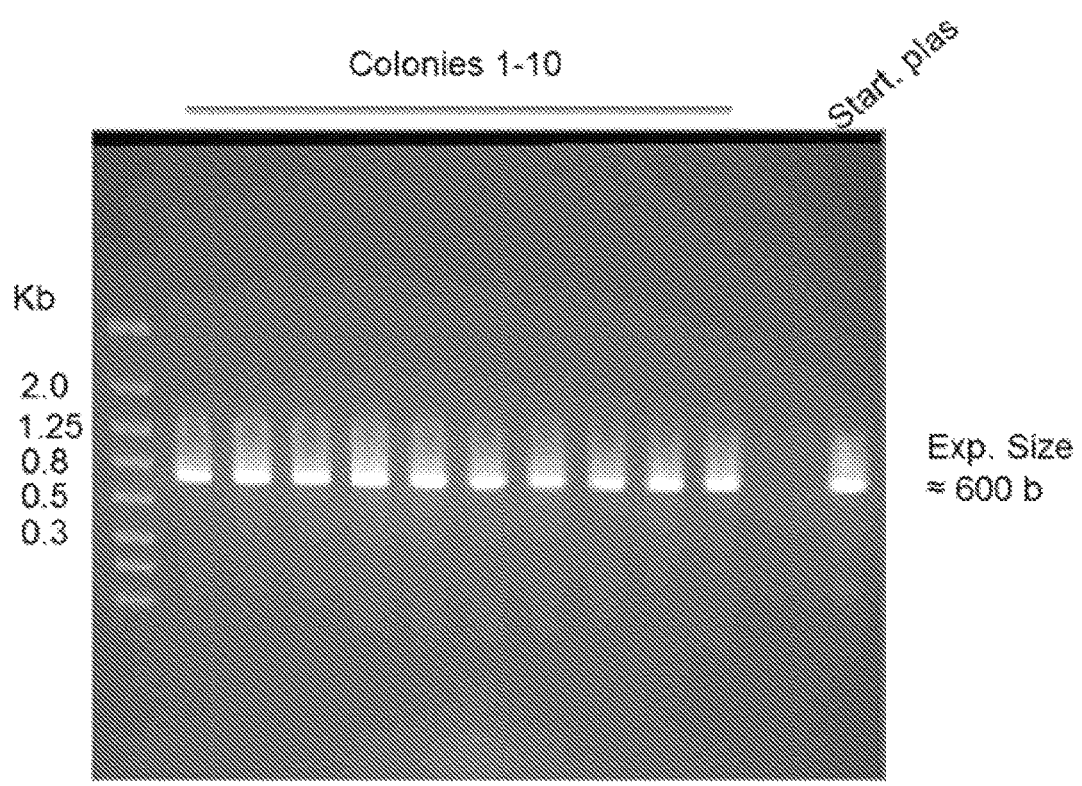
FIG. 7 shows the presence of the suppressor tRNA plasmid in a glnA auxotrophic strain cultured by continuous fermentation over a period of 5 days.

Example 7. Continuous Fermentation of a glnA Auxotrophic Strain Carrying a Complementaing Auxotrophic Plasmid This example describes continuous fermentation of an auxotrophic strain over a period of 5 days. Strain SBDG226 was made by knocking out the chromosomal copy of glnA from the parental *E. coli* strain as described above. SBDG226 was transformed with a pACYC-based plasmid carrying the glnA gene under the control of a constitutive promoter (a complementing auxotrophic plasmid) as described above. The plasmid also contained an amber suppressor tRNA expression cassette comprising a promoter, terminator and the amber suppressor tRNA gene. The transformed SBDG226 was grown overnight in LB with kanamycin and then was used to inoculate modified 80-80 media containing reduced glucose in a bioreactor with controlled temperatures, pH and dissolved $O_2$. After the sugar was consumed in the batch phase, DM 80-80 media with standard sugar concentrations was fed through at a constant rate to maintain the $OD_{600}$ of the bioreactor while the bioreactor was emptied at this same rate. DM 80-80 media (a chemically defined synthetic media) does not contain glutamine, which allows for auxotrophic maintenance of the suppressor tRNA plasmid during batch and continuous growth. Cells propagated during the continuous fermentation phase were assayed for the correct plasmid using PCR to amplify the tRNA gene using standard techniques. The results show that the complementing auxotrophic plasmid was stable in the cells for at least 5 days (FIG. 7). The plasmid was maintained in all the colonies. This example illustrates that auxotrophic selection plasmids are stable and maintained in auxotrophic transformants propagated by continuous fermentation in defined media.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for maintaining an auxotrophic selection plasmid within the cytosol of a population of *E. coli* cells, wherein the doubling rate of the cell population is less than 60 minutes, the method comprising:
   (i) transforming an auxotrophic strain of *E. coli*, wherein said strain comprises an inactivated glnA gene and wherein said glnA gene is necessary for the biosynthesis of glutamine, with the auxotrophic selection plasmid having an expression cassette comprising a constitutive promoter operably linked to the glnA gene; and
   (ii) culturing the transformed *E. coli* of step (i) in a growth media comprising glutamine, thereby applying selective pressure to maintain the auxotrophic selection plasmid within the cytosol of the *E. coli* cell population,
   wherein the doubling rate of the *E. coli* cell population is less than 60 minutes.

2. The method of claim 1, wherein said population is lysed after culturing.

3. The method of claim 1, wherein the auxotrophic selection plasmid is a multicopy plasmid.

4. The method of claim 1, wherein the auxotrophic selection plasmid comprises a strong constitutive promoter.

5. The method of claim 1, wherein the *E. coli* cells have an inactivated gene encoding a protein selected from the group consisting of tryptophanase, arginine decarboxylase, L-serine deaminase and gamma-glutamylcysteine synthase.

6. The method of claim 1, wherein the auxotrophic selection plasmid further comprises an expression cassette comprising a gene encoding a chaperone protein or a tRNA.

7. The method of claim 6, wherein the chaperone protein is selected from the group consisting of DsbA, DsbB, DsbC, DsbD, FkpA, SlyD, and a combination thereof.

8. The method of claim 6, wherein the tRNA is a suppressor tRNA.

9. A high-growth capacity, auxotrophic strain of *E. coli* cells wherein the strain:
   (i) has an inactivated gene necessary for the synthesis of glutamine;
   (ii) is transformed with an auxotrophic selection plasmid having an expression cassette comprising a constitutive promoter operably linked to the glnA gene; and
   (iii) has a doubling rate of less than 60 minutes in a growth media comprising glutamine.

10. The strain of claim 9, wherein the inactivated gene is glnA.

11. The strain of claim 9, wherein the auxotrophic selection plasmid is a multicopy plasmid.

12. The strain of claim 9, wherein the *E. coli* cells have an inactivated gene encoding a protein selected from the group consisting of tryptophanase, arginine decarboxylase, L-serine deaminase and gamma-glutamylcysteine synthase.

13. The strain of claim 9, wherein the auxotrophic selection plasmid further comprises an expression cassette comprising a gene encoding a chaperone protein or a tRNA.

14. The strain of claim 13, wherein the chaperone protein is selected from the group consisting of DsbA, DsbB, DsbC, DsbD, FkpA, SlyD, and a combination thereof.

15. The strain of claim 13, wherein the tRNA is a suppressor tRNA.

16. A method for preparing a bacterial cell extract for use in an in vitro protein expression reaction, comprising:
   (i) culturing an *E. coli* cell in a growth media comprising glutamine, wherein
      (a) a gene that is necessary for the biosynthesis of glutamine has been inactivated in the *E. coli* cell;
      (b) the *E. coli* cell comprises an auxotrophic selection plasmid having an expression cassette comprising a constitutive promoter operably linked to the glnA gene; and
      (c) the doubling rate of a population of the *E. coli* cell is less than 60 minutes; and
   (ii) preparing a bacterial cell extract of the culture.

17. The method of claim 16, wherein the step of preparing the bacterial cell extract of the culture comprises lysing the *E. coli* cell.

18. The method of claim 16, wherein the inactivated gene is glnA.

19. The method of claim 16, wherein the auxotrophic selection plasmid is a multicopy plasmid.

20. The method of claim 16, wherein the *E. coli* cell has an inactivated gene encoding a protein selected from the group consisting of tryptophanase, arginine decarboxylase, L-serine deaminase and gamma-glutamylcysteine synthase.

21. The method of claim 16, wherein the auxotrophic selection plasmid further comprises an expression cassette comprising a gene encoding a chaperone protein or a tRNA.

22. The method of claim 21, wherein the chaperone protein is selected from the group consisting of DsbA, DsbB, DsbC, DsbD, FkpA, SlyD, and a combination thereof.

23. The method of claim 21, wherein the tRNA is a suppressor tRNA.

* * * * *